(12) United States Patent
Sackstein

(10) Patent No.: US 8,765,126 B2
(45) Date of Patent: Jul. 1, 2014

(54) METHODS OF TREATING COMPLICATIONS AND DISORDERS ASSOCIATED WITH G-CSF ADMINISTRATION

(76) Inventor: Robert Sackstein, Sudbury, MA (US)

( * ) Notice: Subject to any disclaimer, the term of this patent is extended or adjusted under 35 U.S.C. 154(b) by 0 days.

(21) Appl. No.: 13/465,691

(22) Filed: May 7, 2012

(65) Prior Publication Data

US 2013/0224217 A1    Aug. 29, 2013

Related U.S. Application Data

(60) Provisional application No. 61/482,784, filed on May 5, 2011.

(51) Int. Cl.
*A61K 39/395* (2006.01)
(52) U.S. Cl.
USPC ................. 424/130.1; 424/146.1; 424/152.1; 424/153.1
(58) Field of Classification Search
None
See application file for complete search history.

(56) References Cited

U.S. PATENT DOCUMENTS

| | | | |
|---|---|---|---|
| 6,210,670 B1 * | 4/2001 | Berg | 424/153.1 |
| 2008/0221133 A1 * | 9/2008 | Tiden | 514/263.34 |
| 2012/0039888 A1 * | 2/2012 | Frenette et al. | 424/138.1 |

OTHER PUBLICATIONS

Kuligowski et al., (Blood. Jun. 18, 2009;113(25):6485-6494).*
Nagao et al., (Nephrol Dial Transplant. Jan. 2007;22(1):77-87).*

* cited by examiner

*Primary Examiner* — Daniel C Gamett
(74) *Attorney, Agent, or Firm* — Bryan Cave LLP

(57) ABSTRACT

The present embodiments relate to novel uses of MPO inhibitors and inhibitors of MPO and E-selectin binding. In some embodiments, methods are provided for treating G-CSF-induced vascular complications and associate tissue injury comprising administering to a subject in need thereof a compound that inhibits E-selectin receptor/ligand interaction or inhibits MPO activity. The inhibitors may be administered in conjunction with G-CSF therapy. The inhibitors include antibody molecules, as well as homologues, analogues and modified or derived forms thereof, including immunoglobulin fragments like Fab, F(ab')$_2$ and Fv, small molecules, including peptides, oligonucleotides, peptidomimetics (including aptamers) and organic compounds (e.g., glycomimetics).

14 Claims, 17 Drawing Sheets

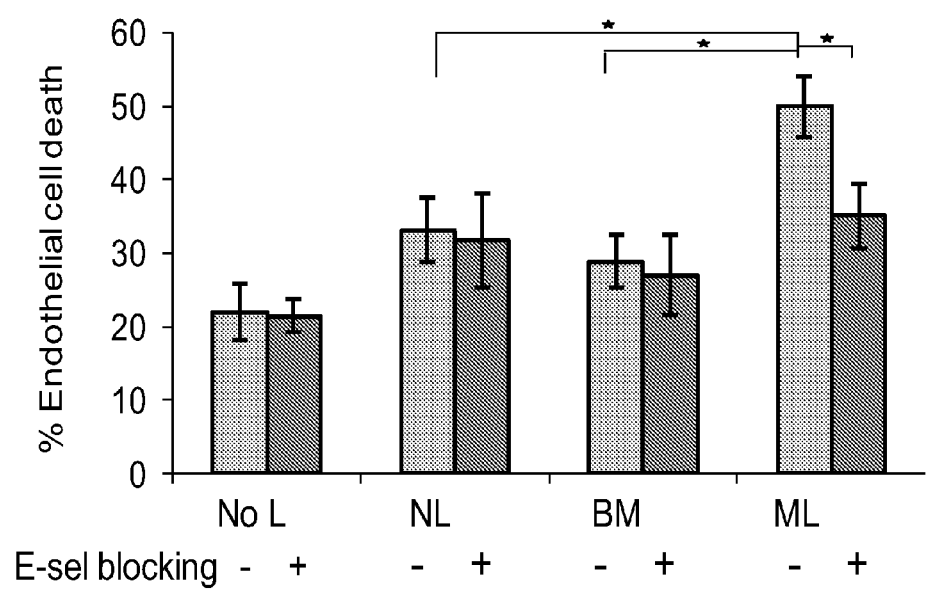

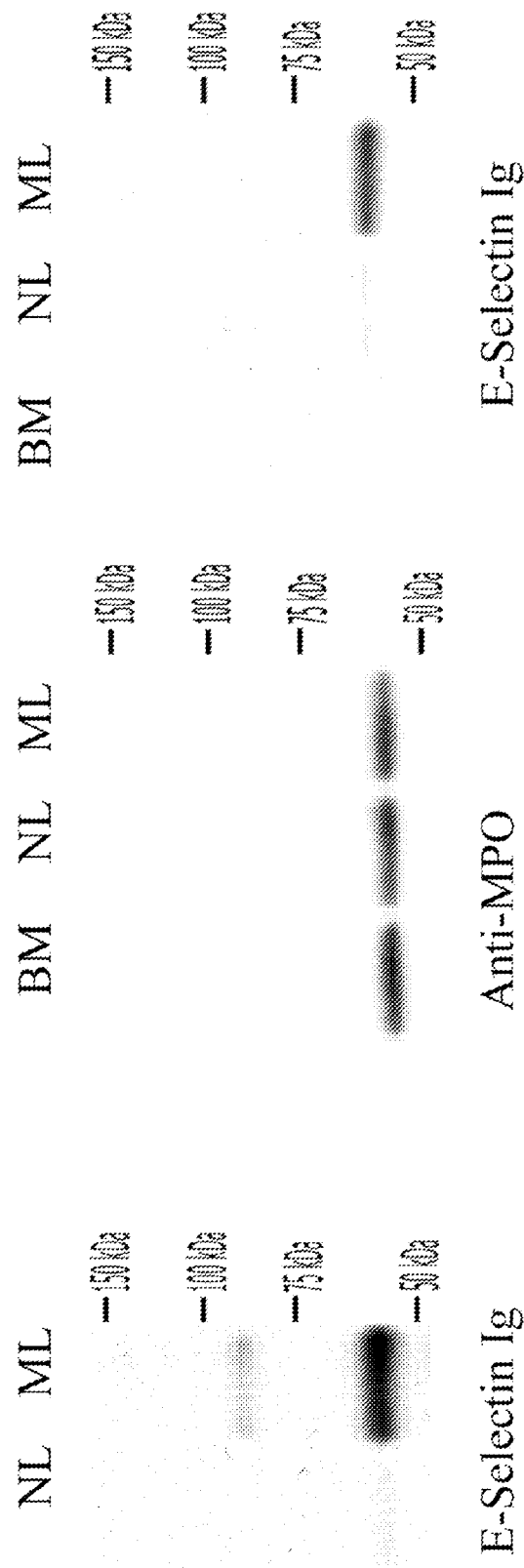

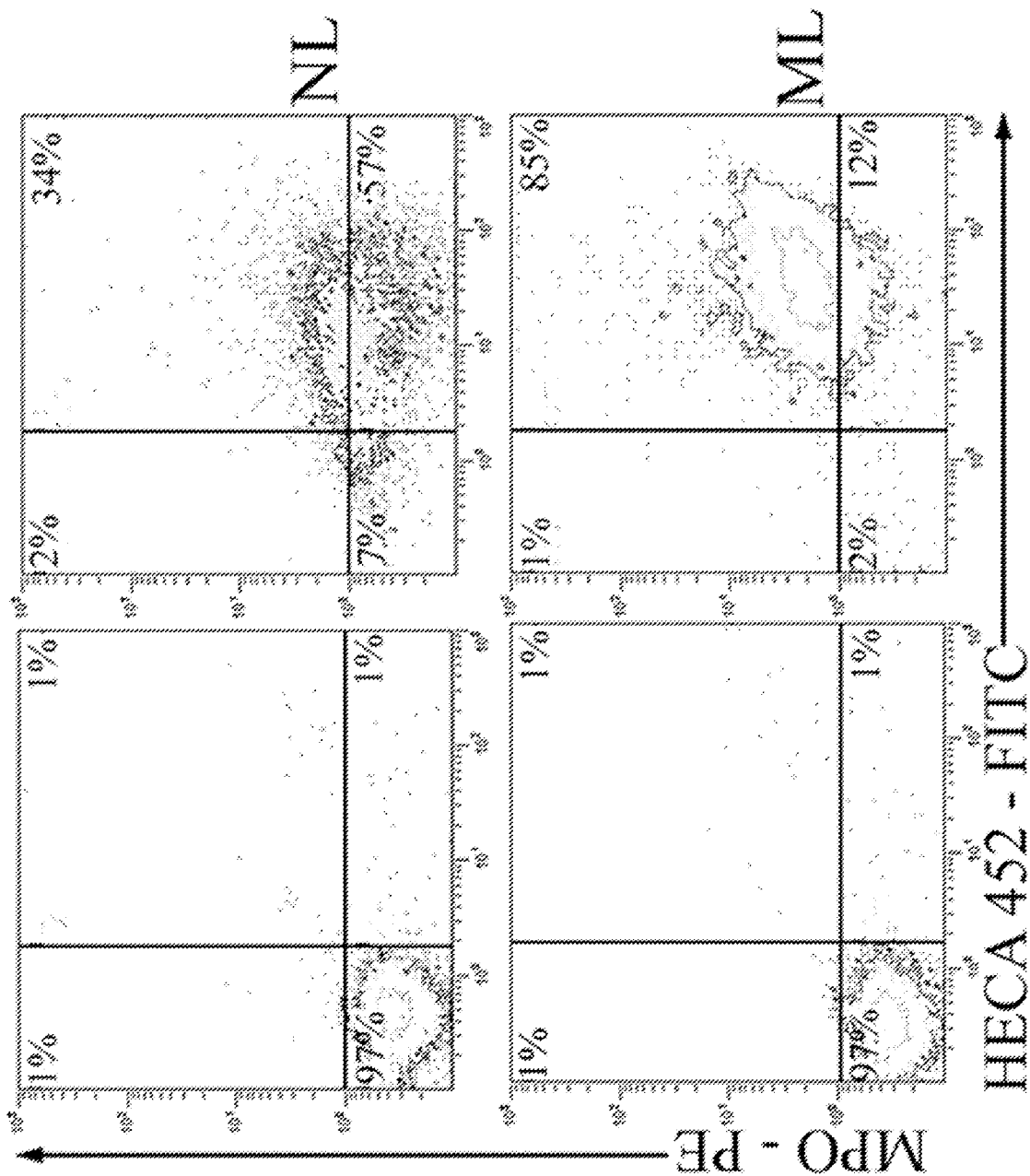

Figure 5C-D
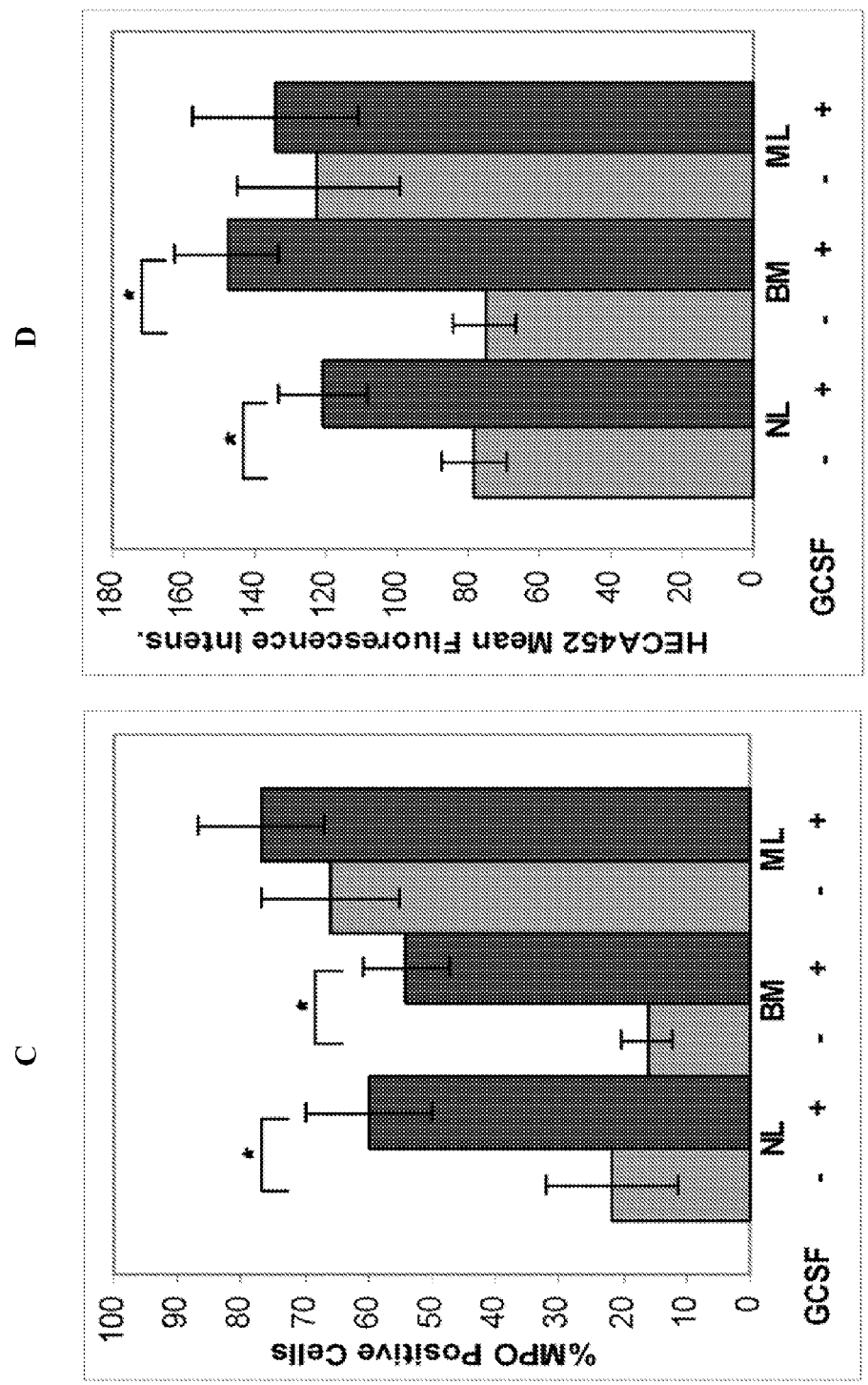

METHODS OF TREATING COMPLICATIONS AND DISORDERS ASSOCIATED WITH G-CSF ADMINISTRATION

RELATED APPLICATIONS

This application claims the benefit of priority to U.S. Provisional Application No. 61/482,784, filed May 5, 2011, incorporated herein by reference in its entirety.

STATEMENT OF GOVERNMENT INTEREST

This invention was made with Government support under grant numbers RO1 HL073714 and RO1 HL060528 awarded by the National Institutes of Health. The Government has certain rights in the invention.

FIELD OF THE DISCLOSURE

Embodiments of the present disclosure are directed to compositions and methods of treating complications and disorders associated with G-CSF administration.

BACKGROUND OF THE DISCLOSURE

The host defense response is critically linked to induction of vascular adhesion molecules and chemoattractants which recruit leukocytes to pertinent inflammatory sites. Leukocyte migration to tissues is tightly regulated in order to ensure optimal delivery of microbicidal products. This process begins with tethering and rolling of leukocytes on the endothelial lining at the target tissue, followed by activation of integrins and firm adhesion to the vessel wall, culminating in transendothelial migration. The initial shear-resistant adherence of leukocytes to the endothelial surface is mediated by selectin receptor/ligand interactions. The selectin family consists of "leukocyte-specific" L-selectin and "vascular selectins" P- and E-selectin, each of which binds sialofucosylated determinants, prototypically displayed as sialyl Lewis x (sLex). On human hematopoietic cells, two glycoproteins decorated with sialofucosylated glycans and recognized by mAb HECA-452 have been characterized as major counter-receptors for the vascular selectins: a glycoform of P-selectin glycoprotein ligand-1 (PSGL-1) called Cutaneous Lymphocyte Antigen (CLA) and a glycoform of CD44 known as Hematopoietic Cell E-/L-selectin Ligand (HCELL).

Activated leukocytes entering an inflammatory site employ various cytotoxic mechanisms including generation of reactive oxygen species (ROS). Phagocytosis induces a respiratory burst accompanied by creation of superoxide anion ($O_2^-$) and hydrogen peroxide ($H_2O_2$). The lysosomal enzyme myeloperoxidase (MPO) then uses hydrogen peroxide together with halide electron donors ($Cl^-$, $I^-$) to synthesize toxic and more efficient ROS like hypohalous acids (HClO, HIO). It is thought that extracellular leakage/release of toxic oxidants damages surrounding tissue, including endothelium, resulting in vascular inflammatory conditions such as leukocytoclastic vasculitis, systemic vasculitis syndromes, and atherosclerosis.

Granulocyte colony-stimulating factor (G-CSF or GCSF) is a hematopoietic cytokine that stimulates leukocyte production and activation. G-CSF serves a key role in host defense, and its expression is markedly upregulated in response to inflammatory insults. G-CSF is commonly used therapeutically to stimulate myelopoiesis after chemo- and/or radio-therapy and to mobilize progenitor cells for hematopoietic stem cell transplantation (HSCT). Though generally safe, use of this cytokine can be associated with significant vascular complications, including angina pectoris and myocardial infarct, sickle cell vaso-occlusion, splenic rupture, and leukocytoclastic vasculitis. Indeed, cutaneous leukocytoclastic vasculitis has been observed in as many as 6% of patients receiving G-CSF, and G-CSF administration is known to induce flares of systemic vasculitis and localized vasculitis (e.g., uveitis).

Following G-CSF administration for mobilization of hematopoietic stem cells, circulating myeloid cells exhibit increased adhesive interactions with cytokine-stimulated vascular endothelium when compared to native leukocytes (NL). These G-CSF-mobilized leukocytes (ML) display increased E-selectin ligand activity resulting from G-CSF-induced expression of Golgi glycosyltransferases which control synthesis of sLex. Conspicuously, G-CSF induces expression of a novel E-selectin ligand, a glycoprotein with electrophoretic mobility of ~65 kDa.

There is increasing evidence of vascular complications, including angina pectoris, myocardial infarct, and early restenosis of vascular stents, associated with clinical G-CSF administration. G-CSF has gained wide therapeutic use for hastening recovery of neutropenia induced by radiotherapy and/or chemotherapy, in treatment of cyclic neutropenia, and for mobilization of bone marrow progenitors for hematopoietic stem cell transplantation. Moreover, this agent is being considered for treatment of non-hematologic indications, including immunomodulation and neuroprotection. Accordingly, there remains a need to critically examine and prevent the negative effect(s) of G-CSF administration on vascular/tissue integrity, while retaining intended salutary effect(s). More generally, there is a need to identify molecular effectors of vascular/tissue injury that accompany release of myeloid cells from the marrow, and to therapeutically prevent these vasculopathic and organopathic effects.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

SUMMARY OF THE DISCLOSURE

The present application describes a novel composition of the lysosomal enzyme, MPO. The present application also provides description of G-CSF-dependent toxicity that is mediated by induction of MPO expression. Furthermore, the embodiments relate to novel uses of MPO inhibitors and inhibitors of MPO and E-selectin binding. The inhibitors include antibody molecules, as well as homologues, analogues and modified or derived forms thereof, including immunoglobulin fragments like Fab, $F(ab')_2$ and Fv, small molecules, including peptides, oligonucleotides, peptidomimetics (including aptamers) and organic compounds (e.g., glycomimetics).

Embodiments of the present disclosure are directed to compositions of matter and to methods of treating complications and disorders associated with leukocyte expression of a sialofucosylated glycoform of myeloperoxidase (MPO) that serves as a potent E-selectin ligand. This molecule is known as MPO-E-selectin Ligand (MPO-EL). MPO-EL may be present on myeloid cells because of a genetic propensity. Most commonly, MPO-EL is induced on myeloid cells by G-CSF administration and is also expressed on myeloid cells in leukemoid reactions (i.e., reactive leukocytosis).

According to some embodiments, methods are provided for treating vascular complications arising from myeloid cell MPO-EL expression comprising administering to a subject in need thereof a compound that inhibits the interaction between E-selectin receptor and an MPO (such as MPO-EL), wherein the compound is an anti-MPO-EL antibody; in treatment of G-CSF-induced vascular complications, this compound is administered in conjunction with G-CSF therapy. In some embodiments, the compound is administered prior to, during or after administration of G-CSF. In some embodiments, the compound is given in absence of exogenous G-CSF administration, such as in cases of leukemoid reactions or certain leukemias (e.g., acute myelogenous leukemia M3). In some embodiments, the subject is a human. In some embodiments, the MPO or MPO-EL is human MPO or human MPO-EL.

According to some embodiments, methods are provided for treating G-CSF-induced vascular complications comprising administering to a subject in need thereof an inhibitor of myeloperoxidase enzymatic activity, wherein the inhibitor is administered in conjunction with G-CSF therapy. In some embodiments, the compound is administered prior to, during or after administration of G-CSF.

According to some embodiments, methods are provided for treating G-CSF-induced vascular complications comprising administering to a subject in need thereof a compound that inhibits the interaction between E-selectin receptor and an MPO (such as MPO-EL), wherein the compound is an anti-MPO-EL antibody, and wherein the compound is administered in conjunction with G-CSF therapy. In some embodiments, the compound is administered prior to, during or after administration of G-CSF. In some embodiments, the subject is a human. In some embodiments, the MPO or MPO-EL is human MPO or human MPO-EL.

According to some embodiments, methods are provided for preventing and/or treating G-CSF-induced vascular complications comprising administering to a subject in need thereof an inhibitor of myeloperoxidase enzymatic activity, wherein the inhibitor is administered in conjunction with G-CSF therapy. In some embodiments, the compound is administered prior to, during or after administration of G-CSF.

According to some embodiments, methods are provided for treating vascular complications comprising administering to a subject in need thereof a compound that inhibits the interaction between E-selectin receptor and MPO-EL. In some embodiments, the compound that inhibits the interaction between E-selectin receptor and MPO-EL is an anti-MPO-EL antibody. In some embodiments, the subject is a human. In some embodiments, the MPO-EL is human MPO-EL.

According to some embodiments, methods are provided for treating vascular complications comprising administering to a subject in need thereof an inhibitor of MPO-EL enzymatic activity. In some embodiments, the subject is a human. In some embodiments, the MPO-EL is human MPO-EL.

According to some embodiments, methods are provided for preventing and/or treating G-CSF-induced inflammatory complications comprising administering to a subject in need thereof an inhibitor of myeloperoxidase enzymatic activity, wherein the inhibitor is administered in conjunction with G-CSF therapy. In some embodiments, the compound is administered prior to, during or after administration of G-CSF.

According to some embodiments, methods are provided for preventing and/or treating G-CSF-induced inflammatory complications comprising administering to a subject in need thereof a compound that inhibits the interaction between E-selectin receptor and MPO-EL. In some embodiments, the compound that inhibits the interaction between E-selectin receptor and MPO-EL is an anti-MPO-EL antibody. In some embodiments, the subject is a human. In some embodiments, the MPO-EL is human MPO-EL.

According to some embodiments, methods are provided for preventing and/or treating G-CSF-induced inflammatory complications comprising administering to a subject in need thereof an inhibitor of MPO-EL enzymatic activity. In some embodiments, the subject is a human. In some embodiments, the MPO-EL is human MPO-EL.

In some embodiments, the complication is sepsis.

In some embodiments, the complication is leukocytoclastic vasculitis.

In some embodiments, the complication is angina pectoris.

In some embodiments, the complication is myocardial infarct.

In some embodiments, the complication is systemic vasculitis syndromes.

In some embodiments, the complication is localized vasculitis syndromes.

In some embodiments, the complication is stroke.

In some embodiments, the complication is atherosclerosis.

In some embodiments, the complication is Wegener's granulomatosis.

In some embodiments, the complication is sickle cell crises.

According to some embodiments, methods are provided for treating G-CSF-induced vascular complications and associated tissue injury comprising administering to a subject in need thereof an inhibitor of myeloperoxidase enzymatic activity, wherein the inhibitor is administered in conjunction with G-CSF therapy. In some embodiments, the compound is administered prior to, during or after administration of G-CSF.

According to some embodiments, methods are provided for treating G-CSF-induced vascular complications and associated tissue injury comprising administering to a subject in need thereof a compound that inhibits the interaction between E-selectin receptor and an MPO (such as MPO-EL), wherein the compound is an anti-MPO-EL antibody, and wherein the compound is administered in conjunction with G-CSF therapy. In some embodiments, the compound is administered prior to, during or after administration of G-CSF.

According to some embodiments, methods are provided for treating G-CSF-induced vascular complications and associated tissue injury comprising administering to a subject in need thereof an inhibitor of myeloperoxidase enzymatic activity, wherein the inhibitor is administered in conjunction with G-CSF therapy. In some embodiments, the compound is administered prior to, during or after administration of G-CSF.

According to some embodiments, methods are provided for treating vascular complications and associated tissue injury comprising administering to a subject in need thereof a compound that inhibits the interaction between E-selectin receptor and MPO-EL. In some embodiments, the compound that inhibits the interaction between E-selectin receptor and MPO-EL is an anti-MPO-EL antibody.

According to some embodiments, methods are provided for treating vascular complications and associated tissue injury comprising administering to a subject in need thereof an inhibitor of MPO-EL enzymatic activity. According to some embodiments, a method is provided for treating myocardial infarction comprising administering to a subject in need thereof an inhibitor of MPO-EL enzymatic activity.

According to some embodiments, a method is provided for treating myocardial infarction and myocardial ischemia comprising administering to a subject in need thereof a compound that inhibits the interaction between E-selectin receptor and MPO-EL. In some embodiments, the compound is an anti-MPO-EL antibody.

According to some embodiments, a method is provided for preventing the occurrence of restenosis at a vascular site of a subject in need thereof comprising administering to a subject in need thereof an inhibitor of MPO-EL enzymatic activity.

According to some embodiments, a method is provided for preventing the occurrence of restenosis at a vascular site of a subject in need thereof comprising administering to a subject in need thereof a compound that inhibits the interaction between E-selectin receptor and MPO-EL. In some embodiments, the compound is an anti-MPO-EL antibody.

According to some embodiments, a method is provided for treating acute myocardial infarction or other ischemic events in conjunction with reperfusion therapy comprising administering to a subject in need thereof a compound that inhibits the interaction between E-selectin receptor and MPO-EL. In some embodiments, the compound is an anti-MPO-EL antibody.

According to some embodiments, a method is provided for treating acute myocardial infarction or other ischemic events in conjunction with reperfusion therapy comprising administering to a subject in need thereof an inhibitor of MPO-EL enzymatic activity.

DETAILED DESCRIPTION OF THE INVENTION

Figure 1A:
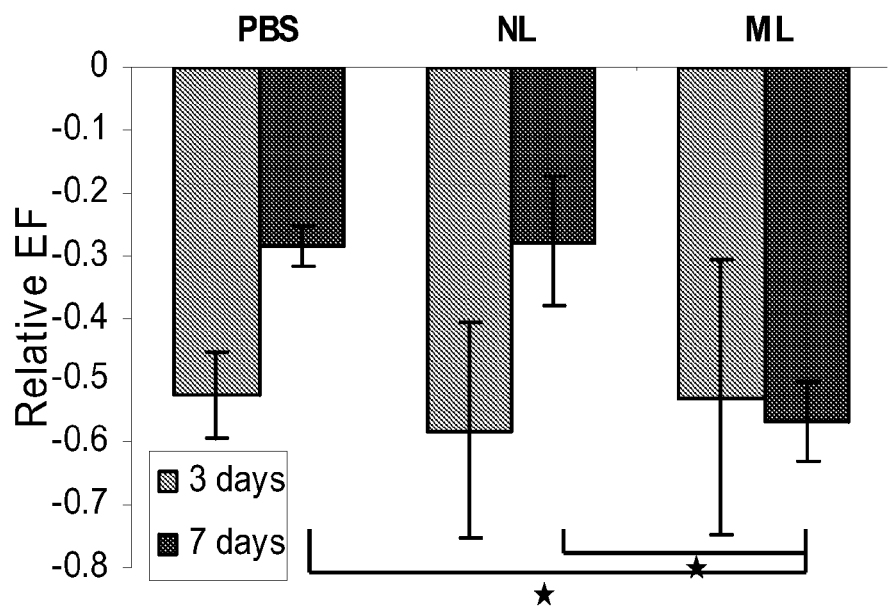
FIGS. 1 A-C. G-CSF-mobilized leukocytes depress cardiac function in mouse myocardial infarct model and exhibit exaggerated angiotoxicity which is mediated by E-selectin receptor/ligand interactions. (A) Relative change in the heart ejection fraction (EF) of induced-myocardial infarct mice injected with PBS, NL or ML with respect to the heart ejection fraction of sham-operated counterpart mice injected with PBS, NL or ML. Values represent mean±SD of percent EF change (n ≥3) registered after 3 days or 7 days post myocardial infarct, *p<0.05. (B) Endothelial cell death evaluated in TNFα-stimulated HUVEC monolayers in the absence of input leukocytes (No L) or in the presence of NL or ML. (C) Endothelial cell death in TNFα-stimulated HUVEC monolayers was monitored after 48 h incubation with NL, BM cells, and ML, or with growth media alone (No L; control), in the absence (−) or presence (+) of function-blocking anti-E-selectin antibodies. Values represent mean±SD of percent endothelial cell death (n=10 donors of NL, BM and ML; brackets show statistically significant differences, * p<0.05).

The present application describes a composition of matter, a novel glycoform of MPO that is expressed as a catalytically-active membrane molecule that binds to E-selectin. This molecule is known as MPO-E-selectin Ligand (MPO-EL). The application also relates to the use of inhibitors of E-selectin receptor/ligand interactions and inhibitors of myeloperoxidase (MPO) and MPO-mediated cytotoxcity in the treatment and prevention of vascular inflammatory conditions and related tissue injury. In some embodiments, the interruption of E-selectin receptor/ligand interactions or inhibition of myeloperoxidase activity will be of clinical benefit in ameliorating not only G-CSF-induced vascular complications, but, also, sepsis, sickle cell crises, atherosclerosis, and systemic vasculitic syndromes such as Wegener's granulomatosis.

According to some embodiments, methods are provided for treating vascular complications and attendant tissue injury arising from myeloid cell MPO-EL expression comprising administering to a subject in need thereof a compound that inhibits the interaction between E-selectin receptor and an MPO (such as MPO-EL). In some embodiments, the compound is an anti-MPO-EL antibody. Where the treatment is related to G-CSF-induced vascular complications, this compound is administered in conjunction with G-CSF therapy. In some embodiments, the compound is administered prior to, during or after administration of G-CSF. In some embodiments, the compound is given in absence of exogenous G-CSF administration, such as in cases of leukemoid reactions or certain leukemias (e.g., acute myelogenous leukemia M3). In some embodiments, the subject is a human. In some embodiments, the MPO or MPO-EL is human MPO or human MPO-EL.

According to some embodiments, methods are provided for treating G-CSF-induced vascular complications and attendant tissue injury by administering to a subject in need thereof inhibitors of E-selectin receptor/ligand interactions. In some embodiments, the inhibitors of E-selectin receptor/ligand interactions are inhibitors of E-selectin receptor/MPO interactions. In some embodiments, the inhibitors of E-selectin receptor/ligand interactions are inhibitors of E-selectin receptor/MPO-EL interactions. In some embodiments, the subject is a human subject.

According to some embodiments, methods are provided for treating G-CSF-induced vascular complications and attendant tissue injury by administering to a subject inhibitors of MPO enzymatic activity. In some embodiments, the MPO is human MPO or human MPO-EL.

In some embodiments, an inhibitor of the present embodiments is administered in conjunction with G-CSF therapy. In some embodiments, the inhibitor is administered to a subject prior to receiving G-CSF therapy. In some embodiments, the inhibitor is administered to a subject simultaneously with G-CSF therapy. In some embodiments, the inhibitor is administered to a subject after receiving G-CSF therapy. In some embodiments, the inhibitor is given to a person suffering from sepsis, sickle cell disease, or collagen vascular disease, such as Wegener's granulomatosis.

According to some embodiments, methods are provided for treating vascular complications and attendant tissue injury by administering to a subject inhibitors of E-selectin receptor/ligand interactions. In some embodiments, the inhibitors of E-selectin receptor/ligand interactions are inhibitors of E-selectin receptor/MPO interactions. In some embodiments, the inhibitors of E-selectin receptor/ligand interactions are inhibitors of E-selectin receptor/MPO-EL interactions.

According to some embodiments, methods are provided for treating vascular complications and attendant tissue injury by administering to a subject inhibitors of MPO enzymatic activity. In some embodiments, the MPO is human MPO or human MPO-EL.

In another aspect, the invention features a method for treating a subject who has received, or is scheduled to receive granulocyte colony stimulating factor (G-CSF). The method includes: administering to the subject an agent which inhibits E-selectin-mediated interaction with a selectin ligand. In some embodiments, the selectin ligand is MPO. In some embodiments, the selectin ligand is MPO-EL. In various embodiments, the method reduces side effects due to administration of G-CSF, such as enhanced leukocyte-endothelial interactions that are associated with adverse inflammatory reactions.

Methods of Reducing Inflammation

Inflammation is inhibited (e.g., reduced) by administering to tissue an inhibitor of the present embodiments (e.g., inhibitors of E-selectin receptor/MPO interactions or MPO enzymatic activity). Inhibitors of MPO-EL would affect endothelial beds within tissues at all sites of inflammation. Tissues that may be treated include any tissue subject to inflammation such as a gastrointestinal tissue (e.g., intestinal tissue), a neurologic tissue (e.g., brain), cardiac tissue, skeletal tissue, muscular tissue, an epithelial tissue, an endothelial tissue, a vascular tissue, a connective tissue, an ocular tissue, a genitourinary tissue (e.g., kidney), a pulmonary tissue, a dermal tissue, a lymphatic tissue (e.g., spleen), or a hepatic tissue. For example, the tissue is an epithelial tissue such as an intestinal epithelial tissue, pulmonary epithelial tissue, dermal tissue (i.e., skin), or liver epithelial tissue.

Inhibition of inflammation is characterized by a reduction of redness, pain and swelling of the treated tissue compared to a tissue that has not been contacted with a selectin inhibitor. Tissues are directly contacted with an inhibitor. Alternatively, the inhibitor is administered systemically. The inhibitors of the present embodiments are administered in an amount sufficient to decrease (e.g., inhibit) leukocyte-endothelial interaction.

In some embodiments, the selectin inhibitor is administered to a subject prior to, during or after receiving G-CSF therapy. An inflammatory response is evaluated morphologically by observing tissue damage, localized redness, and swelling of the affected area. Alternatively, an inflammatory response is evaluated by measuring c-reactive protein, or IL-1 in the tissue or in the serum or plasma. Efficaciousness of treatment is determined in association with any known method for diagnosing or treating the particular inflammatory disorder. Alleviation of one or more symptoms of the inflammatory disorder indicates that the compound confers a clinical benefit.

The methods described herein lead to a reduction in the severity or the alleviation of one or more symptoms of an inflammatory disorder. The inflammatory disorder is acute or chronic. For example, the methods described herein reduce the severity of vascular and inflammatory complications associated with G-CSF therapy. Complications associated with G-CSF therapy include, for example, respiratory distress syndrome, angina pectoris, myocardial infarct, cutaneous leukocytoclastic vasculitis, arthritis, precipitate sickle cell vaso-occlusion, and cardiac ischemia. Disorders are diagnosed and or monitored, typically by a physician using standard methodologies.

The subject is preferably a mammal. The mammal can be, e.g., a human, non-human primate, mouse, rat, dog, cat, horse, or cow. The subject suffers from a disorder in which G-CSF therapy is indicated. For example, the subject is receiving or is scheduled to receive a hematopoietic stem cell transplant.

According to some embodiments, methods are provided for the prevention of restenosis, said method comprising administering to a subject in need thereof an inhibitor of MPO, an inhibitor of MPO or MPO-EL, or an inhibitor of MPO-EL and E-Selectin.

In some embodiments, methods are provided for at least slowing the progression of, if not preventing the occurrence of, restenosis at a vascular site of a host. In the some embodiments, the target vascular site is treated with an inhibitor of MPO, an inhibitor of MPO-EL, or an inhibitor of MPO-EL and E-Selectin for a period of time sufficient for the progression of restenosis at the target site to at least be slowed.

The target vascular site that is contacted with the inhibitors of the present embodiments during the subject methods is one that has been previously treated for vascular occlusion, where the occlusion may be a partial or total occlusion. As such, the target vascular site is one that has the potential for restenosis, i.e. renarrowing of the vessel walls. The target vessel may be an artery or vein, and is usually an artery. The vascular site may be a peripheral or coronary vascular site, where the term peripheral is used broadly to refer to any site that is not a coronary vascular site. As such, peripheral vascular sites include not only limbic vascular sites but also core body vascular sites, e.g. carotid arteries, renal arteries, etc. In certain embodiments, the vascular site is a limbic peripheral vascular site, by which is meant that the vessel in which the vascular site is located is a vessel found in one of the extremities of the patient to be treated, i.e. the arms or legs. Often, the vascular site is a site in a lower extremity vessel, e.g. a lower extremity artery. As indicated above, of particular interest in certain embodiments are peripheral arterial vascular sites, where specific peripheral arteries of interest include: iliac arteries, femoropopliteal arteries, infrapopliteal arteries, femoral arteries, superficial femoral arteries, popliteal arteries, and the like. In yet other embodiments, the vascular site is present in a heart associated vessel, e.g. the aorta, a coronary artery or branch vessel thereof, etc. In yet other embodiments, the vascular site is present in a carotid artery or a branch vessel thereof.

The vascular site is characterized by having been treated for vessel narrowing or occlusion prior to practice of the subject methods. The vessel may have been treated for a total or partial occlusion, where the nature of the occlusion may vary greatly. Thus, the vessel may have been subject to an angioplasty or atherectomy procedure, where the initial vessel narrowing lesion has been manipulated in some fashion to enhance the blood flow rate through the vascular site. For example, the vascular site may be one that has been subjected to balloon angioplasty. Alternatively, the vascular site may be one that has been subjected to mechanical removal of at least a portion of the initially present lesion. In any event, the vascular site is one that is at least potentially subject to vessel renarrowing or reconstriction. In other words, the target vascular site is a site that has a propensity for vessel renarrowing, i.e. restenosis, to occur.

According to some embodiments, there is provided methods of using an inhibitor of MPO, an inhibitor of MPO-EL, or an inhibitor of MPO-EL and E-Selectin in conjunction with reperfusion therapy in the treatment of acute myocardial infarction or other ischemic events. This treatment can be used alone or in combination with other well-known methods of treatment.

More particularly, the invention provides methods of treating acute myocardial infarction (AMI) by the administration of G-CSF polypeptide in conjunction with reperfusion therapy.

According to some embodiments, there is provided methods for the treatment of acute myocardial infarction and myocardial ischemia. In some embodiments, the methods are useful in conjunction with reperfusion therapy for minimizing tissue damage and improving patient outcome after such myocardial injury, illustratively through prevention of cardiac wall thickness loss ordinarily attending ischemia in affected tissues.

In one aspect, therefore, methods are provided for treating AMI to reduce heart damage. Such a method generally would comprise administering an effective amount of a composition comprising a an inhibitor of MPO, an inhibitor of MPO-EL, or an inhibitor of MPO-EL and E-Selectin to a subject in need thereof, including humans, commencing before, concurrently with, and/or after reperfusion therapy.

In another aspect, methods are provided for treating an ischemic injury. Such a method generally would comprise administering an effective amount of a composition comprising an inhibitor of MPO, an inhibitor of MPO-EL, or an inhibitor of MPO-EL and E-Selectin to a subject in need thereof, commencing before, concurrently with, or after reperfusion therapy. The reperfusion therapy contemplated includes mechanical (primary angioplasty), chemical (administration of a thrombolytic agent), or surgical (coronary bypass surgery) means.

In some embodiments, methods are provided for minimizing tissue damage and improving patient outcome after such myocardial injury. Such a method generally would comprise administering an effective amount of a composition comprising an inhibitor of MPO, an inhibitor of MPO-EL, or an inhibitor of MPO-EL and E-Selectin to a subject in need thereof.

In some embodiments, methods are provided for using an inhibitor of MPO, an inhibitor of MPO-EL, or an inhibitor of MPO-EL and E-Selectin in conjunction with reperfusion therapy protocols for the treatment of AMI. The present section provides an overview of the events which take place in myocardial infarction and reperfusion to the extent that such a description will facilitate a better understanding of the methods of the present invention.

Occlusion of the left coronary artery due to thrombosis is the major cause of AMI accompanied by ST-segment elevation. The loss of blood flow to the tissue from the inclusion causes damaged myocardium due to ischemia, infarction, necrosis, and scar formation. The expedient restoration of blood flow to the jeopardized area minimizes tissue damage and improves patient outcome. This restoration of blood flow, "reperfusion,", can be accomplished medically, with a thrombolytic agent, or mechanically, with balloon angioplasty or stenting (Lange et al., N. Engl. J. Med. 346:954-955, 2002).

Although reperfusion therapy provides relief to the damaged tissue and inhibits further scarring of the myocardium, the infarcted myocardium does not regenerate. Thus, AMI is a critical event which can lead to progressive heart failure and even death. Therefore, the present invention provides a novel method of using an inhibitor of MPO, an inhibitor of MPO-EL, or an inhibitor of MPO-EL and E-Selectin in conjunction with reperfusion therapy to minimize myocardial damage after AMI.

Myeloperoxidase

Myeloperoxidase (MPO) is a highly characterized glycoprotein well known in the art. MPO is a heme protein synthesized during myeloid differentiation that constitutes the major component of neutrophil azurophilic granules. Produced as a single chain precursor, myeloperoxidase is subsequently cleaved into a light and heavy chain. The mature myeloperoxidase is a tetramer composed of 2 light chains and 2 heavy chains. This enzyme produces hypohalous acids central to the microbicidal activity of netrophils.

The catalytic activity of MPO is located in the heme pocket deeply embedded in the inner protein core (Fiedler et al., J Biol Chem. 2000 Apr. 21; 275(16):11964-71.). N-glycosylation sites are well conserved in the protein, which includes five Asn glycosylation sites (323, 355, 391, 483, and 729) on the heavy polypeptide of MPO. MPO is characterized by rigid heme architecture, as the heme is covalently linked to Asp260, Glu408, and Met409 and the proximal histidine (His502) is hydrogen-bonded with an asparagine (Asn587). The roof of the distal heme pocket is formed by an arginine (Arg405) and the distal histidine (His261) that is close to calcium-binding Asp262. Additional Ca2+-binding residues are found in the sequence Thr334Ser335Phe336Val337Asp338 Ala339Ser340 that is connected to Asn355 by a α-helix. Antwerpen et al., J Biol Chem. 2010 May 21; 285(21): 16351-16359.

The overall protein fold of MPO was first revealed by a 3A resolution crystal structure of the canine enzyme (Protein Data Bank (PDB) code: 1MYP) (Zeng J, Fenna R E. J Mol. Biol. 1992; 226:185-207.). By now, the structure of human MPO at 2.3 Å resolution is solved and refined to 1.8 Å using X-ray data recorded at −180° C. (1CXP) (Fiedler T J, Davey C A, Fenna R E. J Biol Chem. 2000; 275:11964-11971). The structure of MPO and its interaction with bromide (Br—) (1D2V) and thiocyanate (SCN—) (1DNU) (Id., Fiedler et al., 2000) as well as of the MPO-cyanide (MPO—CN—) complex (1D5L) and its interaction with Br— (1D7W) and SCN— (1DNW) was published (Blair-Johnson M, Fiedler T, Fenna R. Biochemistry. 2001; 40:13990-13997). In addition, there is one report on the crystal structure of salicylhydroxamic acid (SHA) bound to human MPO (Davey C A, Fenna R E. Biochemistry. 1996; 35:10967-10973).

MPO-EL, is a glycoform of a well-characterized lysosomal enzyme, myeloperoxidase (MPO). MPO-EL is expressed on the myeloid cell surface and it is catalytically active (i.e., as a myeloperoxidase). MPO-EL binds E-selectin (an endothelial molecule), which means that a cytotoxic molecule (MPO) is now capable of attaching directly to the endothelium. This kills the endothelial cell, and leads to vascular complications. Inhibitors (or antagonists) of MPO-EL block the cytotoxic activity by reducing MPO activity and/or reducing the interaction between MPO-EL and E-selectin binding. Inhibitors include antibodies to E-selectin, or small molecules that block E-selectin receptor/ligand interactions (e.g., GMI-1070)).

MPO Antibodies

According to some embodiments, the inhibitor of E-selectin receptor/ligand interactions suitable for use in the methods of the present embodiments is an anti-MPO antibody. In some embodiments, the MPO is human MPO or human MPO-EL.

In some embodiments, the inhibitor of E-selectin receptor/MPO interactions suitable for use in the methods of the present embodiments is an anti-MPO antibody. In some embodiments, the inhibitor of MPO enzymatic activity suitable for use in the methods of the present embodiments is an anti-MPO antibody.

In some embodiments, the inhibitor of E-selectin receptor/MPO-EL interactions suitable for use in the methods of the present embodiments is an anti-MPO-EL antibody. In some embodiments, the inhibitor of MPO enzymatic activity suitable for use in the methods of the present embodiments is an anti-MPO-EL antibody.

The present disclosure provides antibodies that specifically bind to MPO or MPO-EL. MPO antibodies suitable for use in the present application are disclosed in U.S. Publication No. 20090148866 and U.S. Publication No. 20080286818, the disclosures of which are incorporated herein by reference in their entireties.

As used herein, the terms "antibody" and "antibodies" refer to monoclonal antibodies, multispecific antibodies, human antibodies, humanized antibodies (fully or partially humanized), animal antibodies such as, but not limited to, a bird (for example, a duck or goose), a shark or whale, a mammal, including a non-primate (for example, a cow, pig, camel, llama, horse, goat, rabbit, sheep, hamsters, guinea pig, cat, dog, rat, mouse, etc) or a non-human primate (for example, a monkey, such as a cynomologous monkey, a chimpanzee, etc), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies (including, for example, anti-Id antibodies to antibodies of the present disclosure), and functionally active epitope-binding fragments of any of the above.

In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$, and IgA$_2$) or subclass. An antibody whose affinity (namely, K$_D$, k$_D$ or k$_a$) has been increased or improved via the screening of a combinatory antibody library that has been prepared using bio-display, is referred to herein as an "affinity maturated antibody". For simplicity sake, an antibody against a protein is frequently referred to herein as being either an "anti-protein antibody", or merely a "protein antibody" (e.g., an MPO antibody or an anti-MPO antibody).

Methods of Making and Using MPO Antibodies

The antibodies of the present disclosure can be made using a variety of different techniques known in the art. For example, polyclonal and monoclonal antibodies against MPO can be raised by immunizing a suitable subject (such as, but not limited to, a rabbit, goat, mouse or other mammal) with an immunogenic preparation which contains a suitable immunogen, such as purified MPO antigen. For example, a suitable immunogen can be MPO purified from human neutrophils.

The antibodies raised in the subject can then be screened to determine if the antibodies bind to MPO. Such antibodies can be further screened to identify antibodies that inhibit MPO binding or interaction with E-selectin. Antibodies can be further screened to identify antibodies that inhibit MPO activity. Suitable methods to identify an antibody with the desired characteristics are described herein (See, Examples section). In some embodiments, the assay involves assessing whether there was diminished death of cytokine-activated endothelial cells (e.g., using tumor necrosis factor alpha (TNFα) to upregulate endothelial E-selectin expression) by MPO-EL-expressing myeloid cells (i.e., G-CSF-treated myeloid cells). Data provided herein shows that inhibition of MPO function or of E-selectin receptor/ligand interactions blunts MPO-EL-mediated cytotoxicity. Agents may be screened for their ability to disrupt MPO-EL-mediated cytotoxicity.

In some embodiments, there is provided methods of screening for agents that block MPO-EL enzymatic activity using the methods disclosed herein.

In some embodiments, there is provided methods of screening for agents that block MPO-EL and E-selectin receptor binding activity using the methods disclosed herein.

In some embodiments, there is provided methods of screening for agents that block MPO-EL and E-selectin receptor binding activity comprising assessing whether there is diminished death of cytokine-activated endothelial cells (e.g., using tumor necrosis factor alpha (TNFa) to upregulate endothelial E-selectin expression) by MPO-EL-expressing myeloid cells (i.e., G-CSF-treated myeloid cells).

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed MPO-EL glycoprotein or a chemically synthesized MPO polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against HCELL can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of MPO. A monoclonal antibody composition thus typically displays a single binding affinity for a particular MPO glycoprotein with which it immunoreacts. For preparation of monoclonal antibodies directed towards a particular MPO glycoprotein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 Nature 256: 495-497); the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96). Each of the above citations are incorporated herein by reference in their entirety.

According to the invention, techniques can be adapted for the production of single-chain antibodies specific to a MPO (see e.g., U.S. Pat. No. 4,946,778). In addition, methodologies can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a MPO or derivatives, fragments, analogs or homologs thereof. Non-human antibodies can be "humanized" by techniques well known in the art. See e.g., U.S. Pat. No. 5,225,539. Antibody fragments that contain the idiotypes to a MPO may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-MPO antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173, 494; PCT International Publication No. WO 86/01533; U.S. Pat. Nos. 4,816,567; 5,225,539; European Patent Application No. 125,023; Better et al. (1988) Science 240:1041-1043; Liu et al. (1987) PNAS 84:3439-3443; Liu et al. (1987) J Immunol. 139:3521-3526; Sun et al. (1987) PNAS 84:214-218; Nishimura et al. (1987) Cancer Res 47:999-1005; Wood et al. (1985) Nature 314:446-449; Shaw et al. (1988) J Natl Cancer Inst 80:1553-1559); Morrison (1985) Science 229:1202-1207; Oi et al. (1986) BioTechniques 4:214; Jones et al. (1986) Nature 321:552-525; Verhoeyan et al. (1988) Science 239:1534; and Beidler et al. (1988) J Immunol 141:4053-4060. Each of the above citations are incorporated herein by reference in their entirety.

Human monoclonal antibodies can be produced by introducing an antigen into immune deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (See, for example, WO 93/05796, U.S. Pat. No. 5,411,749; or McCune et al., Science, 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a MPO is facilitated by generation of hybridomas that bind to the fragment of a MPO possessing such a domain. Antibodies that are specific for a N-linked glycosylation site, or derivatives, fragments, analogs or homologs thereof, are also provided herein.

In a given embodiment, antibodies for MPO, or derivatives, fragments, analogs or homologs thereof, that contain the antibody derived binding domain, are utilized as pharmacologically-active compounds [hereinafter "Therapeutics"].

Generation of Monoclonal Antibodies (MAbs) to Human MPO

In one embodiment of the invention, anti-MPO MAbs can be raised by immunizing rodents (e.g. mice, rats, hamsters and guinea pigs) with either native MPO purified from human plasma or urine, or recombinant MPO or its fragments expressed by either eukaryotic or prokaryotic systems. Other animals can be used for immunization, e.g. non-human primates, transgenic mice expressing human immunoglobulins and severe combined immunodeficient (SCID) mice transplanted with human B lymphocytes. Hybridomas can be generated by conventional procedures by fusing B lymphocytes from the immunized animals with myeloma cells (e.g. Sp2/0 and NS0), as described by G. Kohler and C. Milstein (Nature, 1975:256:495-497). In addition, anti-MPO antibodies can be generated by screening of recombinant single-chain Fv or Fab libraries from human B lymphocytes in phage-display systems. The specificity of the MAbs to human MPO can be tested by enzyme linked immunosorbent assay (ELISA), Western immunoblotting, or other immunochemical techniques. The inhibitory activity of the antibodies on complement activation can be assessed by hemolytic assays using unsensitized rabbit or guinea pig red blood cells (RBCs) for the alternative pathway, and using sensitized chicken or sheep RBCs for the classical pathway. The hybridomas in the positive wells are cloned by limiting dilution. The antibodies are purified for characterization for specificity to human MPO by the assays described above.

If used in treating diseases in humans, the anti-MPO antibodies would preferably be used as chimeric, deimmunized, humanized or human antibodies. Such antibodies can reduce immunogenicity and thus avoid human anti-mouse antibody (HAMA) response. It is preferable that the antibody be IgG4, IgG2, or other genetically mutated IgG or IgM which does not augment antibody-dependent cellular cytotoxicity (S. M. Canfield and S. L. Morrison, J. Exp. Med., 1991:173:1483-1491) and complement mediated cytolysis (Y. Xu et al., J. Biol. Chem., 1994:269:3468-3474; V. L. Pulito et al., J. Immunol., 1996; 156: 2840-2850).

Chimeric antibodies are produced by recombinant processes well known in the art, and have an animal variable region and a human constant region. Humanized antibodies have a greater degree of human peptide sequences than do chimeric antibodies. In a humanized antibody, only the complementarity determining regions (CDRs) which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. See L. Riechmann et al., Nature, 1988; 332: 323-327; G. Winter, U.S. Pat. No. 5,225,539; C. Queen et al., U.S. Pat. No. 5,530,101.

Deimmunized antibodies are antibodies in which the T and B cell epitopes have been eliminated, as described in International Patent Application PCT/GB98/01473. They have no immunogenicity, or reduced immunogenicity, when applied in vivo.

Human antibodies can be made by several different ways, including by use of human immunoglobulin expression libraries (Stratagene Corp., La Jolla, Calif.) to produce fragments of human antibodies (VH, VL, Fv, Fd, Fab, or F(ab')$_2$), and using these fragments to construct whole human antibodies using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J.

One can also create single peptide chain binding molecules in which the heavy and light chain Fv regions are connected. Single chain antibodies ("ScFv") and the method of their construction are described in U.S. Pat. No. 4,946,778. Alternatively, Fab can be constructed and expressed by similar means (M. J. Evans et al., J. Immunol. Meth., 1995; 184: 123-138). All of the wholly and partially human antibodies are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary. In addition, the smaller size of the antibody fragment may help improve tissue bioavailability, which may be critical for better dose accumulation in acute disease indications.

Inhibitors of Myeloperoxidase

Derivatives of Thioxanthines

According to some embodiments, the inhibitor of E-selectin receptor/ligand interactions suitable for use in the methods of the present embodiments is a derivative of thioxanthine.

In some embodiments, the inhibitor of E-selectin receptor/MPO-EL interactions suitable for use in the methods of the present embodiments is a derivative of thioxanthine. In some embodiments, the inhibitor of MPO enzymatic activity suitable for use in the methods of the present embodiments is a derivative of thioxanthine.

In some embodiments, the inhibitor of E-selectin receptor/MPO-EL interactions suitable for use in the methods of the present embodiments is a derivative of thioxanthine. In some embodiments, the inhibitor of MPO enzymatic activity suitable for use in the methods of the present embodiments is a derivative of thioxanthine.

Derivatives of thioxanthine suitable for use in the methods of the present embodiments are disclosed in U.S. Publication No. 2008/0293748, U.S. Pat. Nos. 8,026,244, 7,943,625, 7,425,560, each of which are incorporated herein by reference in their entireties.

In some embodiments, the thioxanthine derivative for use in the methods of the present embodiments is a compound according to following Formula (I):

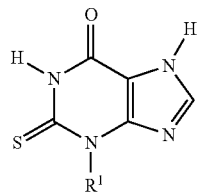

(I)

wherein $R^1$ is selected from $C_1$-$C_6$ alkyl, and said $C_1$-$C_6$ alkyl is substituted with $C_1$-$C_6$ alkoxy; and at least one of said $C_1$-$C_6$ alkyl or said $C_1$-$C_6$ alkoxy is branched; or a pharmaceutically acceptable salt thereof, solvate or solvate of a salt thereof.

In some embodiments, the $C_1$-$C_6$ alkyl of $R^1$ represents $C_{2-4}$alkyl. In some embodiments, the alkyl is selected from isobutyl, ethyl and propyl. In some embodiments, the alkyl is substituted with $C_{1-3}$alkoxy. In some embodiments, the alkyl is substituted with $C_1$-alkoxy. In some embodiments, the alkyl is substituted with $C_2$-alkoxy. In some embodiments, the alkyl is substituted with propoxy or iso-propoxy.

In some embodiments, the thioxanthine derivative for use in the methods of the present embodiments is a compound selected from the group consisting of: 3-(2-Ethoxy-2-methylpropyl)-2-thioxanthine; 3-(2-Propoxy-2-methylpropyl)-2-thioxanthine; 3-(2-Methoxy-2-methylpropyl)-2-thioxanthine; 3-(2-isopropoxyethyl)-2-thioxanthine; 3-(2-Ethoxypropyl)-2-thioxanthine; 3-(2S-Ethoxypropyl)-2-thioxanthine; 3-(2R-Ethoxypropyl)-2-thioxanthine; or a pharmaceutically acceptable salt, solvate or solvate of a salt thereof.

With regard to Formula I, the term "$C_1$-$C_6$ alkyl" referred to herein denotes a straight or branched chain alkyl group having from 1 to 6 carbon atoms. Examples of such groups include methyl, ethyl, n-propyl, n-butyl, iso-butyl, tert-butyl, pentyl and hexyl.

With regard to Formula I, the term "$C_2$-$C_4$ alkyl" is to be interpreted analogously. It is to be understood that when the alkyl denotes a $C_1$ or a $C_2$ alkyl, such alkyls cannot be branched.

With regard to Formula I, the term "$C_1$-$C_6$ alkoxy" referred to herein denotes a straight or branched chain alkoxy group having from 1 to 6 carbon atoms. Examples of such groups include methoxy, ethoxy, 1-propoxy, 2-propoxy, 1-butoxy, iso-butoxy, tert-butoxy and pentoxy.

With regard to Formula I, the term "$C_1$-$C_3$ alkoxy" is to be interpreted analogously. It is to be understood that when the alkoxy denotes a $C_1$ or a $C_2$-alkoxy, such alkoxys cannot be branched.

In some embodiments, the thioxanthine derivative for use in the methods of the present embodiments is a compound according to following Formulas (Ia) or (Ib):

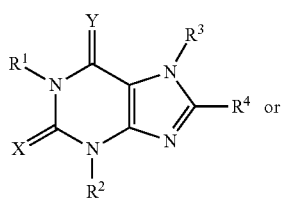

(Ia)

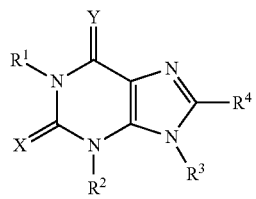

(Ib)

wherein:
one of X and Y represents S, and the other represents O or S; $R^1$ represents hydrogen or C1 to 6 alkyl; $R^2$ represents hydrogen or C1 to 6 alkyl; said alkyl group being optionally substituted by:

i) a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy; or ii) C1 to 6 alkoxy; or iii) an aromatic ring selected from phenyl, furyl or thienyl; said aromatic ring being optionally further substituted by halogen, C1 to 6 alkyl or C1 to 6 alkoxy; $R^3$ and $R^4$ independently represent hydrogen or C1 to 6 alkyl; or a pharmaceutically acceptable salt thereof.

The compounds of formulas I, Ia or Ib may exist in enantiomeric forms. Therefore, all enantiomers, diastereomers, racemates and mixtures thereof are included within the scope of the invention.

It will be appreciated that when $R^3$ in formulae (Ia) and (Ib) represents hydrogen, the two alternative representations (Ia) and (Ib) are tautomeric forms of the same compound. All such tautomers and mixtures of tautomers are included within the scope of the present invention.

In some embodiments, the thioxanthine derivative for use in the methods of the present embodiments is a compound according to formula (Ia) or (Ib) wherein at least one of X and Y represents S, and the other represents O or S; $R^1$ represents hydrogen or C1 to 6 alkyl; $R^2$ represents hydrogen or C1 to 6 alkyl; said alkyl group being optionally substituted by C3 to 7 cycloalkyl, C1 to 4 alkoxy, or an aromatic ring selected from phenyl, furyl or thienyl; said aromatic ring being optionally further substituted by halogen, C1 to 4 alkyl or C1 to 4 alkoxy; $R^3$ and $R^4$ independently represent hydrogen or C1 to 6 alkyl; or a pharmaceutically acceptable salt, enantiomer or racemate thereof.

In some embodiments, the thioxanthine derivative for use in the methods of the present embodiments is a compound according to formula (Ia) or (Ib) wherein at least one of X and Y represents S, and the other represents O or S; $R^1$ represents hydrogen or C1 to 6 alkyl; $R^2$ represents hydrogen or C1 to 6 alkyl; said alkyl group being optionally substituted by: i) a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 4 alkoxy; or ii) C1 to 4 alkoxy; or iii) an aromatic ring selected from phenyl, furyl or thienyl; said aromatic ring being optionally further substituted by halogen, C1 to 4 alkyl or C1 to 4 alkoxy; $R^3$ and $R^4$ independently represent hydrogen or C1 to 6 alkyl.

In some embodiments, the thioxanthine derivative for use in the methods of the present embodiments is a compound according to compounds of formula (Ia) or (Ib) wherein X represents S and Y represents 0.

In another embodiment, $R^3$ in formula (Ia) or (Ib) represents hydrogen.

In another embodiment, $R^2$ in formula (Ia) or (Ib) represents optionally substituted C1 to 6 allyl.

In another embodiment, $R^2$ in formula (Ia) or (Ib) represents C1 to 6 alkyl substituted by a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy.

In another embodiment, $R^2$ in formula (Ia) or (Ib) represents methylene, ethylene or trimethylene substituted by cyclopropyl, cyclohexyl, tetrahydrofuranyl or morpholinyl.

In another embodiment, $R^2$ in formula (Ia) or (Ib) represents C1 to 6 alkyl substituted by C1 to 6 alkoxy.

In another embodiment, $R^2$ in formula (Ia) or (Ib) represents ethylene or trimethylene substituted by methoxy or ethoxy.

When X represents S and Y represents O, a further embodiment comprises compounds of formula (Ia) or (Ib) wherein $R^1$ represents hydrogen.

When X represents S and Y represents O, a yet further embodiment comprises compounds of formula (Ia) or (Ib) wherein $R^4$ represents hydrogen.

When X represents 0 and Y represents S, a further embodiment comprises compounds of formula (Ia) or (Ib) wherein $R^1$ represents C1 to 6 alkyl.

When X represents 0 and Y represents S, a yet further embodiment comprises compounds of formula (Ia) or (Ib) wherein $R^4$ represents C1 to 6 alkyl.

In one embodiment, the invention relates to the use of compounds of formula (Ia) or (Ib) wherein X represents S and Y represents O; $R^2$ represents optionally substituted C1 to 6 alkyl; and $R^1$, $R^3$ and $R^4$ each represent hydrogen.

In one embodiment, the invention relates to the use of compounds of formula (Ia) or (Ib) herein X represents S and Y represents O; $R^2$ represents C1 to 6 alkyl substituted by a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy; and $R^1$, $R^3$ and $R^4$ each represent hydrogen.

In one embodiment, the invention relates to the use of compounds of formula (Ia) or (Ib) wherein X represents S and Y represents O; $R^2$ represents C1 to 6 alkyl substituted by C1 to 6 alkoxy; and $R^1$, $R^3$ and $R^4$ each represent hydrogen.

In some embodiments, the thioxanthine derivative for use in the methods of the present embodiments is a compound selected from the groups consisting of: 1,3-diisobutyl-8-methyl-6-thioxanthine; 1,3-dibutyl-8-methyl-6-thioxanthine; 3-isobutyl-1,8-dimethyl-6-thioxanthine; 3-(2-methylbutyl)-6-thioxanthine; 3-isobutyl-8-methyl-6-thioxanthine; 3-isobutyl-2-thioxanthine; 3-isobutyl-2,6-dithioxanthine; 3-isobutyl-8-methyl-2-thioxanthine; 3-isobutyl-7-methyl-2-thioxanthine; 3-cyclohexylmethyl-2-thioxanthine; 3-(3-methoxypropyl)-2-thioxanthine; 3-cyclopropylmethyl-2-thioxanthine; 3-isobutyl-1-methyl-2-thioxanthine; 3-(2-tetrahydrofuryl-methyl)-2-thioxanthine; 3-(2-methoxyethyl)-2-thioxanthine; 3-(3-(1-morpholinyl)-propyl)-2-thioxanthine; 3-(2-furyl-methyl)-2-thioxanthine; 3-(4-methoxybenzyl)-2-thioxanthine; 3-(4-fluorobenzyl)-2-thioxanthine; 3-phenethyl-2-thioxanthine; (+)-3-(2-tetrahydrofuryl methyl)-2-thioxanthine; (−)-3-(2-tetrahydrofuryl-methyl)-2-thioxanthine; 3-n-butyl-2-thioxanthine; 3-n-propyl-2-thioxanthine; 3-isobutyl-6-thioxanthine; 2-thioxanthine; and pharmaceutically acceptable salts thereof.

With regard to formula (Ia) or (Ib), unless otherwise indicated, the term "C1 to 6 alkyl" referred to herein denotes a straight or branched chain alkyl group having from 1 to 6 carbon atoms. Examples of such groups include methyl, ethyl, 1-propyl, n-butyl, iso-butyl, tert-butyl, pentyl and hexyl.

With regard to formula (Ia) or (Ib), term "C1 to 4 alkyl" is to be interpreted analogously.

With regard to formula (Ia) or (Ib), the term "C3 to 7 cycloalkyl" referred to herein denotes a cyclic alkyl group having from 3 to 7 carbon atoms. Examples of such groups include cyclopropyl, cyclopentyl and cyclohexyl.

With regard to formula (Ia) or (Ib), unless otherwise indicated, the term "C1 to 6 alkoxy" referred to herein denotes a straight or branched chain alkoxy group having from 1 to 6 carbon atoms. Examples of such groups include methoxy, ethoxy, 1-propoxy, 2-propoxy and tert-butoxy.

With regard to formula (Ia) or (Ib), term "C1 to 4 alkoxy" is to be interpreted analogously.

With regard to formula (Ia) or (Ib), unless otherwise indicated, the term "halogen" referred to herein denotes fluoro, chloro, bromo and iodo.

Examples of a saturated or partially unsaturated 3- to 7-membered ring optionally incorporating one or two heteroatoms selected independently from O, N and S, and optionally incorporating a carbonyl group include cyclopropyl, cyclopentyl, cyclohexyl, cyclopentanone, tetrahydrofuran, pyrrolidine, piperidine, morpholine, piperazine, pyrrolidinone and piperidinone. Particular examples include cyclopropyl, cyclohexyl, tetrahydrofuranyl(tetrahydrofuryl) and morpholinyl.

Derivatives of pyrrolo[3,2-d]pyrimidin-4-one derivatives

According to some embodiments, the inhibitor of E-selectin receptor/ligand interactions suitable for use in the methods of the present embodiments is a derivative of pyrrolo[3,2-d]pyrimidin-4-one.

In some embodiments, the inhibitor of E-selectin receptor/MPO-EL interactions suitable for use in the methods of the present embodiments is a derivative of benzothiophene. In some embodiments, the inhibitor of MPO enzymatic activity suitable for use in the methods of the present embodiments is a derivative of pyrrolo[3,2-d]pyrimidin-4-one.

In some embodiments, the inhibitor of E-selectin receptor/MPO-EL interactions suitable for use in the methods of the present embodiments is a derivative of benzothiophene. In some embodiments, the inhibitor of MPO enzymatic activity suitable for use in the methods of the present embodiments is a derivative of pyrrolo[3,2-d]pyrimidin-4-one.

Derivatives of pyrrolo[3,2-d]pyrimidin-4-one suitable for use in the methods of the present embodiments are disclosed in U.S. Pat. No. 7,829,707, incorporated herein by reference in its entirety.

In some embodiments, the pyrrolo[3,2-d]pyrimidin-4-one derivative for use in the methods of the present embodiments is a compound according to the following Formula II:

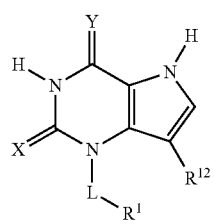

wherein:

at least one of X and Y represents S, and the other represents O or S; L represents a direct bond or C1 to 7 alkylene, said alkylene optionally incorporating a heteroatom selected from O, S(O)$_n$ and NR$^6$, said alkylene optionally incorporating one or two carbon-carbon double bonds, and said alkylene being optionally substituted by one or more substituents selected independently from OH, halogen, CN and NR$^4$R$^5$, C1 to 6 alkyl and C1 to 6 alkoxy, said alkoxy optionally incorporating a carbonyl adjacent to the oxygen; n represents an integer 0, 1 or 2; R$^1$ represents hydrogen, or i) a saturated or partially unsaturated 3 to 7 membered ring optionally incorporating one or two heteroatoms selected independently from O, N and S, and optionally incorporating a carbonyl group, optionally substituted by one or more substituents independently selected from halogen, SO$_2$R$^9$, SO$_2$NR$^9$R$^{10}$, OH, C1 to 7 alkyl, C1 to 7 alkoxy, CN, CONR$^2$R$^3$, NR$^2$COR$^3$ and COR$^3$, said alkoxy being optionally further substituted by C1 to 6 alkoxy and said alkoxy optionally incorporating a carbonyl adjacent to the oxygen, and said alkyl being optionally further substituted by hydroxy or C1 to 6 alkoxy and said alkyl or alkoxy optionally incorporating a carbonyl adjacent to the oxygen or at any position in the alkyl; or ii) an aromatic ring system selected from phenyl, biphenyl, naphthyl or a monocyclic or bicyclic heteroaromatic ring structure containing 1 to 3 heteroatoms independently selected from O, N and S, said aromatic ring system being optionally substituted by one or more substituents independently selected from halogen, SO$_2$R$^9$, SO$_2$NR$^9$R$^{10}$, OH, C1 to 7 alkyl, C1 to 7 alkoxy, CN, CONR$^2$R$^3$, NR$^2$COR$^3$ and COR$^3$; said alkoxy being optionally further substituted by C1 to 6 alkoxy and said alkoxy optionally incorporating a carbonyl adjacent to the oxygen, and said alkyl being optionally further substituted by hydroxy or C1 to 6 alkoxy and said alkyl or alkoxy optionally incorporating a carbonyl adjacent to the oxygen or at any position in the alkyl; R$^{12}$ represents hydrogen or halogen or a carbon optionally substituted with one to three halogen atoms; at each occurrence, R$^2$, R$^3$, R$^4$, R$^5$, R$^6$, R$^9$ and R$^{10}$ independently represent hydrogen, C1 to 6 alkyl or C1 to 6 alkoxy said alkoxy optionally incorporating a carbonyl adjacent to the oxygen, said alkyl being optionally further substituted by halogen, C1 to 6 alkoxy, CHO, C2 to 6 alkanoyl, OH, CONR$^7$R$^8$ and NR$^7$COR$^8$; or the groups NR$^2$R$^3$, NR$^4$R$^5$ and NR$^9$R$^{10}$ each independently represent a 5 to 7 membered saturated azacyclic ring optionally incorporating one additional heteroatom selected from O, S and NR$^{11}$, said ring being optionally further substituted by halogen, C1 to 6 alkoxy, CHO, C2 to 6 alkanoyl, OH, CONR$^7$R$^8$ and NR$^7$COR$^8$; at each occurrence R$^7$, R$^8$ and R$^{11}$ independently represent hydrogen or C1 to 6 alkyl, or the group NR$^7$R$^8$ represents a 5- to 7-membered saturated azacyclic ring optionally incorporating one additional heteroatom selected from O, S and NR$^{11}$; and pharmaceutically acceptable salts thereof.

The compounds of formula (II) may exist in enantiomeric forms. It is to be understood that all enantiomers, diastereomers, racemates, tautomers and mixtures thereof are included within the scope of the present embodiments.

The compounds of formula (II) may exist in tautomeric forms. All such tautomers and mixtures of tautomers are included within the scope of the present embodiments.

With regard to Formula II, unless otherwise indicated, the term "C1 to 6 alkyl" referred to herein denotes a straight or branched chain alkyl group having from 1 to 6 carbon atoms. Examples of such groups include, but are not limited to, methyl, ethyl, 1-propyl, n-butyl, iso-butyl, tert-butyl, pentyl and hexyl.

With regard to Formula II, the term "C1 to 7 alkyl" is to be interpreted analogously.

With regard to Formula II, unless otherwise indicated, the term "C1 to 7 alkylene" referred to herein denotes a straight or branched chain alkyl group having from 1 to 7 carbon atoms having two free valencies. Examples of such groups include, but are not limited to, methylene, ethylene, propylene, hexamethylene and ethylethylene.

With regard to Formula II, the term "C1 to 3 alkylene" is to be interpreted analogously.

With regard to Formula II, unless otherwise indicated, the term "C1 to 6 alkoxy" referred to herein denotes a straight or branched chain alkoxy group having from 1 to 6 carbon atoms. Examples of such groups include, but are not limited to, methoxy, ethoxy, 1-propoxy, 2-propoxy(iso-propoxy), tert-butoxy and pentoxy.

With regard to Formula II, the term "C1 to 7 alkoxy" is to be interpreted analogously.

With regard to Formula II, unless otherwise indicated, the term "C2 to 6 alkanoyl" referred to herein denotes a straight or branched chain alkyl group having from 1 to 5 carbon atoms with optional position on the alkyl group by a carbonyl group. Examples of such groups include, but are not limited to, acetyl, propionyl and pivaloyl.

With regard to Formula II, unless otherwise indicated, the term "halogen" referred to herein denotes fluoro, chloro, bromo and iodo.

Examples of a saturated or partially unsaturated 3- to 7-membered ring optionally incorporating one or two heteroatoms selected independently from O, N and S, and optionally incorporating a carbonyl group includes, but is not limited to, cyclopropane, cyclopentane, cyclohexane, cyclohexene, cyclopentanone, tetrahydrofuran, pyrrolidine, piperidine, tetrahydropyridine, morpholine, piperazine, pyrrolidinone and piperidinone.

Examples of a monocyclic or bicyclic heteroaromatic ring structure containing 1 to 3 heteroatoms independently selected from O, N and S includes, but is not limited to, furan, thiophene, pyrrole, oxazole, isoxazole, thiazole, imidazole, pyrazole, triazole, tetrazole, pyridine, pyrazine, pyrimidine, pyridazine, benzofuran, indole, isoindole and benzimidazole.

Examples of a 5 to 7 membered saturated azacyclic ring optionally incorporating one additional heteroatom selected from O, S and NR$^{11}$ includes, but is not limited to, pyrrolidine, piperidine, piperazine, morpholine and thiomorpholine.

In the definition of L, "C1 to 7 alkylene; said alkylene optionally incorporating a heteroatom selected from O, S(O)$_n$ and NR$^6$; said alkylene optionally incorporating one or two carbon-carbon double bonds" embraces a saturated or unsaturated straight or branched chain arrangement of 1 to 7 carbon atoms having two free valencies and in which any two singly bonded carbon atoms are optionally separated by O, S or NR$^6$. The definition thus includes, for example, methylene, ethylene, propylene, hexamethylene, ethylethylene, —CH$_2$=CH$_2$—, —CH$_2$CH=CH—CH$_2$—, —CH(CH$_3$)=CH$_2$—, —CH$_2$=CH$_2$—CH$_2$O—, —CH$_2$O—, —CH$_2$CH$_2$O—CH$_2$—, —CH$_2$CH$_2$O—CH$_2$—CH$_2$—, —CH$_2$CH$_2$S— and —CH$_2$CH$_2$NR$^6$—.

In one embodiment, R$^1$ represents hydrogen.

In another embodiment, X represents S and Y represents O.

In yet another embodiment, Y represents S and X represents O.

In yet another embodiment, L is a direct bond or represents C1 to 7 alkylene, said alkylene optionally incorporating a heteroatom selected from O, S(O)$_n$ and NR$^6$, said alkylene optionally incorporating one or two carbon-carbon double bonds, and said alkylene being optionally substituted by one or more substituents selected independently from OH, C1 to 6 alkoxy, halogen, CN and NR$^4$R$^5$.

In yet another embodiment, L is a direct bond or represents C1 to 7 alkylene; said alkylene being optionally substituted by one or more substituents selected independently from OH, C1 to 6 alkoxy, halogen, CN and NR$^4$R$^5$.

In yet another embodiment, L is a direct bond or represents C1 to 7 alkylene; said alkylene being optionally substituted by one or more C1 to 6 alkoxy.

In yet another embodiment, L is a direct bond or represents C1 to 3 alkylene; said alkylene being optionally substituted by one or more substituents selected independently from OH, C1 to 6 alkoxy, halogen, CN and NR$^4$R$^5$.

In yet another embodiment, L represents C1 to 3 alkylene; said alkylene being optionally substituted by one or more C1 to 6 alkoxy.

In yet another embodiment, L is a direct bond or represents optionally substituted methylene (—CH$_2$—).

In yet another embodiment, L is a direct bond or represents optionally substituted ethylene (—CH$_2$CH$_2$—).

In yet another embodiment, R$^1$ represents a saturated or partially unsaturated 3 to 7 membered ring optionally incorporating one or two heteroatoms selected independently from O, N and S, and optionally incorporating a carbonyl group, said ring being optionally substituted by one or more substituents independently selected from halogen, SO$_2$R$^9$, SO$_2$NR$^9$R$^{10}$, OH, C1 to 6 alkyl, C1 to 6 alkoxy, CN, CONR$^2$R$^3$, NR$^2$COR$^3$ and COR$^3$, said alkoxy being optionally further substituted by C1 to 6 alkoxy; and said alkyl being optionally further substituted by hydroxy or C1 to 6 alkoxy.

In yet another embodiment, R$^1$ represents a saturated or partially unsaturated 3 to 7 membered ring optionally incorporating one or two heteroatoms selected independently from O, N and S, and optionally incorporating a carbonyl group; said ring being optionally substituted by one or more substituents independently selected from halogen, C1 to 6 alkyl and C1 to 6 alkoxy, said alkoxy being optionally further substituted by C1 to 6 alkoxy.

In yet another embodiment, R$^1$ represents an aromatic ring system selected from phenyl, biphenyl, naphthyl or a monocyclic or bicyclic heteroaromatic ring structure containing 1 to 3 heteroatoms independently selected from O, N and S, said aromatic ring being optionally substituted by one or more substituents independently selected from halogen, SO$_2$R$^9$, SO$_2$NR$^9$R$^{10}$, OH, C1 to 6 alkyl, C1 to 6 alkoxy, CN, CONR$^2$R$^3$, NR$^2$COR$^3$ and COR$^3$, said alkoxy being optionally further substituted by C1 to 6 alkoxy, and said alkyl being optionally further substituted by hydroxy or C1 to 6 alkoxy.

In yet another embodiment, R$^1$ represents an aromatic ring system selected from phenyl, biphenyl, naphthyl or a five- or six-membered heteroaromatic ring containing 1 to 3 heteroatoms independently selected from O, N and S, said aromatic ring being optionally substituted by one or more substituents independently selected from halogen, C1 to 6 alkyl and C1 to 6 alkoxy, said alkoxy being optionally further substituted by C1 to 6 alkoxy.

In yet another embodiment, R$^1$ represents an optionally substituted phenyl.

In yet another embodiment, R$^1$ represents an optionally substituted pyridyl.

In yet another embodiment, L represents C1 to 7 alkylene and R$^1$ represents H.

In yet another embodiment, L represents an optionally substituted C1 to 3 alkylene and R$^1$ represents a saturated or partially unsaturated 3- to 7-membered ring optionally incorporating one or two heteroatoms selected independently from O, N and S, and optionally incorporating a carbonyl group, said ring being optionally substituted by one or more substituents independently selected from halogen, SO$_2$R$^9$, SO$_2$NR$^9$R$^{10}$, OH, C1 to 6 alkyl, C1 to 6 alkoxy, CN, CONR$^2$R$^3$, NR$^2$COR$^3$ and COR$^3$, said alkoxy being optionally further substituted by C1 to 6 alkoxy, and said alkyl being optionally further substituted by hydroxy or C1 to 6 alkoxy.

In yet another embodiment, L represents an optionally substituted C1 to 3 alkylene and R$^1$ represents a saturated or partially unsaturated 3- to 7-membered ring optionally incorporating one or two heteroatoms selected independently from O, N and S, and optionally incorporating a carbonyl group, said ring being optionally substituted by one or more substituents independently selected from halogen, C1 to 6 alkyl and C1 to 6 alkoxy, said alkoxy being optionally further substituted by C1 to 6 alkoxy.

In yet another embodiment, L represents optionally substituted C1 to 3 alkylene and R$^1$ represents an aromatic ring system selected from phenyl, biphenyl, naphthyl or a five- or six-membered heteroaromatic ring containing 1 to 3 heteroatoms independently selected from O, N and S; said aromatic ring being optionally substituted by one or more substituents independently selected from halogen, SO$_2$R$^9$, SO$_2$NR$^9$R$^{10}$, OH, C1 to 6 alkyl, C1 to 6 alkoxy, CN, CONR$^2$R$^3$, NR$^2$COR$^3$ and COR$^3$, said alkoxy being optionally further substituted by C1 to 6 alkoxy, and said alkyl being optionally further substituted by hydroxy or C1 to 6 alkoxy.

In yet another embodiment, L represents optionally substituted C1 to 3 alkylene and R$^1$ represents an aromatic ring system selected from phenyl, biphenyl, naphthyl or a five- or six-membered heteroaromatic ring containing 1 to 3 heteroatoms independently selected from O, N and S, said aromatic ring being optionally substituted by one or more substituents independently selected from halogen, C1 to 6 alkyl and C1 to 6 alkoxy, said alkoxy being optionally further substituted by C1 to 6 alkoxy.

In yet another embodiment, X represents S, Y represents O, L represents optionally substituted C1 to 3 alkylene and R$^1$ represents optionally substituted phenyl.

In yet another embodiment, X represents S, Y represents O, L represents optionally substituted C1 to 3 alkylene and R$^1$ represents optionally substituted pyridyl.

In yet another embodiment, X represents S, Y represents O, L represents C1 to 3 alkylene, substituted with C1 to 6 alkoxy and R$^1$ represents hydrogen.

Particular compounds of the invention include: 1-butyl-2-thioxo-1,2,3,5-tetrahydro-pyrrolo[3,2-d]pyrimidin-4-one; 1-isobutyl-2-thioxo-1,2,3,5-tetrahydro-pyrrolo[3,2-d]pyrimidin-4-one; 1-(pyridin-2-ylmethyl)-2-thioxo-1,2,3,5-tetrahydro-pyrrolo[3,2-d]pyrimidi-n-4-one; 1-(2-fluoro-benzyl)-2-thioxo-1,2,3,5-tetrahydro-pyrrolo[3,2-d]pyr-imidin-4-one; 1-[2-(2-methoxyethoxy)-3-propoxybenzyl]-2-thioxo-1,2,3,5-tetrahydro-pyrro-lo[3,2-d]pyrimidin-4-one; 1-(6-ethoxy-pyridin-2-ylmethyl)-2-thioxo-1,2,3,5-tetrahydropyrrolo[3,2-d-]pyrimidin-4-one; 1-piperidin-3-ylmethyl-2-thioxo-1,2,3,5-tetrahydro-pyrrolo[3,2-d]pyrimidi-n-4-one; 1-butyl-4-thioxo-1,3,4,5-tetrahydro-2H-pyrrolo[3,2-d]pyrimidin-2-one; 1-(2-isopropoxyethyl)-2-thioxo-1,2,3,5-tetrahydro-pyrrolo[3,2-d]pyrim-idin-4-one; 1-(2-methoxy-2-methylpropyl)-2-thioxo-1,2,3,5-tetrahydro-pyrrolo[3,2-d]py-rimidin-4-one; 1-(2-ethoxy-2-methylpropyl)-2-thioxo-1,2,3,5-tetrahydro-pyrrolo[3,2-d]pyr-imidin-4-one; 1-(piperidin-4-ylmethyl)-2-thioxo-1,2,3,5-tetrahydro-pyrrolo[3,2-d]pyrimi-din-4-one; 1-[(1-methylpiperidin-3-yl)methyl]-2-thioxo-1,2,3,5-tetrahydro-pyrrolo[3,2-d]pyrimidin-4-one; 1-[2-hydroxy-2-(4-methoxyphenyl)ethyl]-2-thioxo-1,2,3,5-tetrahydro-pyrrol-o[3,2-d]pyrimidin-4-one; 1-(2-methoxybenzyl)-2-thioxo-1,2,3,5-tetrahydro-pyrrolo[3,2-d]pyrimidin-4-one; 1-(3-methoxybenzyl)-2-thioxo-1,2,3,5-tetrahydro-pyrrolo[3,2-d]pyrimi-din-4-one; 1-(2,4-dimethoxybenzyl)-2-thioxo-1,2,3,5-tetrahydro-pyrrolo[3,2-d]pyrimidin-4-one; 1-[(3-chloropyridin-2-yl)methyl]-2-thioxo-1,2,3,5-tetrahydro-pyrrolo[3,2-d]pyrimidin-4-one; 1-{[3-(2-ethoxyethoxy)pyridin-2-yl]methyl}-2-thioxo-1,2,3,5-tetrahydro-py-rrolo[3,2-d]pyrimidin-4-one; 1-[(6-oxo-1,6-dihydropyridin-2-yl)methyl]-2-thioxo-1,2,3,5-tetrahydro-pyr-rolo[3,2-d]pyrimidin-4-one; 1-(1H-indol-3-ylmethyl)-2-thioxo-1,2,3,5-tetrahydro-pyrrolo[3,2-d]pyrimid-in-4-one; 1-(1H-benzimidazol-2-ylmethyl)-2-thioxo-1,2,3,5-tetrahy-dro-pyrro-lo[3,2-d]pyrimidin-4-one; 1-[(5-chloro-1H-indol-2-yl)methyl]-2-thioxo-1,2,3,5-tetrahydro-pyrrolo[3,-2-d]py-rimidin-4-one; 1-[(5-fluoro-1H-indol-2-yl)methyl]-2-thioxo-1,2,3,5-tetrahydro-pyrrolo[3,-2-d]pyrimidin-4-one; 1-(1H-indol-6-ylmethyl)-2-thioxo-1,2,3,5-tetrahydro-pyr-rolo[3,2-d]pyrimid-in-4-one; 1-(1H-indol-5-ylmethyl)-2-thioxo-1,2,3,5-tetrahydro-pyrrolo[3,2-d]pyrimidin-4-one; 1-[(5-fluoro-1H-indol-3-yl)methyl]-2-thioxo-1,2,3,5-tet-rahydro-pyrrolo[3,-2-d]pyrimidin-4-one; 1-(1H-imidazol-5-ylmethyl)-2-thioxo-1,2,3,5-tetrahydro-pyrrolo[3,2-d]pyri-midin-4-one; 1-(1H-imidazol-2-ylmethyl)-2-thioxo-1,2,3,5-tetrahydro-pyrrolo[3,2-d]pyri-midin-4-one; 1-[(5-chloro-1H-benzimidazol-2-yl)methyl]-2-thioxo-1,2,3,5-tetrahydro-pyr-rolo[3,2-d]pyrimidin-4-one; 1-[(4,5-dimethyl-1H-benzimidazol-2-yl)methyl]-2-thioxo-1,2,3,5-tetrahydro-1-pyrrolo[3,2-d]pyrimidin-4-one; 7-bromo-1-isobutyl-2-thioxo-1,2,3,5-tetrahydro-pyrrolo[3,2-d]pyrimidin-4-one; and 1-(3-chlorophenyl)-2-thioxo-1,2,3,5-tetrahydro-pyrrolo[3,2-d]pyri-midin-4-one; and pharmaceutically acceptable salts thereof.

Derivatives of Benzothiophenes

According to some embodiments, the inhibitor of E-selectin receptor/ligand interactions suitable for use in the methods of the present embodiments is a derivative of benzothiophene.

In some embodiments, the inhibitor of E-selectin receptor/MPO-EL interactions suitable for use in the methods of the present embodiments is a derivative of benzothiophene. In some embodiments, the inhibitor of MPO enzymatic activity suitable for use in the methods of the present embodiments is a derivative of benzothiophene.

In some embodiments, the inhibitor of E-selectin receptor/MPO-EL interactions suitable for use in the methods of the present embodiments is a derivative of benzothiophene. In some embodiments, the inhibitor of MPO enzymatic activity suitable for use in the methods of the present embodiments is a derivative of benzothiophene.

Derivatives of benzothiophenes include droloxifene and raloxifene. Derivatives of benzothiophenes include 2-phenyl-3-aroylbenzothiophene derivatives. Derivatives of benzothiophene suitable for use in the methods of the present embodiments are disclosed in U.S. Pat. Nos. 5,708,009, 5,719,190, and European Patent No. EP0664125, each of which are incorporated herein by reference in their entireties.

In some embodiments, the benzothiophene derivative for use in the methods of the present embodiments is a compound according to following Formula (III):

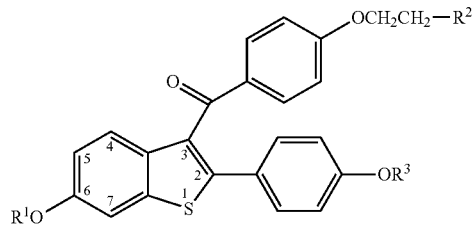

wherein $R^1$ and $R^3$ are independently hydrogen, —$CH_3$,

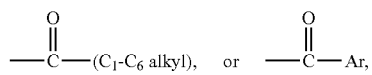

wherein Ar is optionally substituted phenyl; $R^2$ is selected from the group consisting of pyrrolidino, hexamethylene-imino, and piperidino; and pharmaceutically acceptable salts and solvates thereof.

Raloxifene is the hydrochloride salt of a compound of formula III wherein $R^1$ and $R^3$ are hydrogen and $R^2$ is 1-piperidinyl.

In some embodiments, the benzothiophene derivative for use in the methods of the present embodiments is a compound according to following Formula (IIIa):

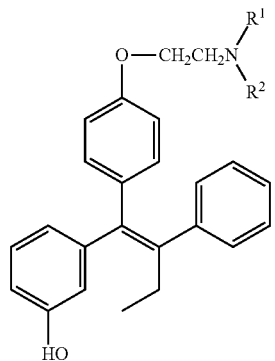

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a benzyl group or a pharmaceutically acceptable salt thereof. A preferred salt is the citrate salt.

A preferred formula I compound is that in which $R^1$ and $R^2$ each are methyl. This preferred compound is known as droloxifene, (E)-1-[4'-(2-Dimethylaminoethoxy)phenyl]-1-(3-hydroxyphenyl)-2-phenylbut-I-ene.

Derivatives of Flavonoids

According to some embodiments, the inhibitor of E-selectin receptor/ligand interactions suitable for use in the methods of the present embodiments is a derivative of flavonoid.

In some embodiments, the inhibitor of E-selectin receptor/MPO-EL interactions suitable for use in the methods of the present embodiments is a derivative of flavonoid. In some embodiments, the inhibitor of MPO enzymatic activity suitable for use in the methods of the present embodiments is a derivative of flavonoid.

In some embodiments, the inhibitor of E-selectin receptor/MPO-EL interactions suitable for use in the methods of the present embodiments is a derivative of flavonoid. In some embodiments, the inhibitor of MPO enzymatic activity suitable for use in the methods of the present embodiments is a derivative of flavonoid.

Derivatives of flavonoids include quercetin.

Derivatives of Fluoroindoles

According to some embodiments, the inhibitor of E-selectin receptor/ligand interactions suitable for use in the methods of the present embodiments is a derivative of fluoroindole.

In some embodiments, the inhibitor of E-selectin receptor/MPO-EL interactions suitable for use in the methods of the present embodiments is a derivative of fluoroindole. In some embodiments, the inhibitor of MPO enzymatic activity suitable for use in the methods of the present embodiments is a derivative of fluoroindole.

In some embodiments, the inhibitor of E-selectin receptor/MPO-EL interactions suitable for use in the methods of the present embodiments is a derivative of fluoroindole. In some embodiments, the inhibitor of MPO enzymatic activity suitable for use in the methods of the present embodiments is a derivative of fluoroindole.

In some embodiments, the derivative of fluoroindole is 3-(aminoalkyl)-5-fluoroindole 3-(aminoalkyl)-5-fluoroindole or analogue. See Soubhye et al., J Med Chem. 2010 Dec. 23; 53(24):8747-59, incorporated herein by reference in its entirety.

Derivatives of Fluorotryptamines

According to some embodiments, the inhibitor of E-selectin receptor/ligand interactions suitable for use in the methods of the present embodiments is a derivative of fluorotryptamine.

In some embodiments, the inhibitor of E-selectin receptor/MPO-EL interactions suitable for use in the methods of the present embodiments is a derivative of fluorotryptamine. In some embodiments, the inhibitor of MPO enzymatic activity suitable for use in the methods of the present embodiments is a derivative of fluorotryptamine.

In some embodiments, the inhibitor of E-selectin receptor/MPO-EL interactions suitable for use in the methods of the present embodiments is a derivative of fluorotryptamine. In some embodiments, the inhibitor of MPO enzymatic activity suitable for use in the methods of the present embodiments is a derivative of fluorotryptamine.

In some embodiments, the derivative of fluorotryptamine is 5-fluorotryptamine.

Sugar Mimetics

According to some embodiments, the inhibitor of E-selectin receptor/ligand interactions suitable for use in the methods of the present embodiments is a Sialyl Lewis X (SLe$^x$) or SLe$^x$-like construct (or SLe$^x$ analog or mimetic), or Sialyl Lewis A (SLe$^a$) or SLe$^a$-like construct. Inhibitors of E-selectin receptor/ligand interactions are disclosed in U.S. Pat. No. 5,972,625, incorporated herein by reference in its entirety.

In some embodiments, the inhibitor of E-selectin receptor/MPO-EL interactions suitable for use in the methods of the present embodiments is an SLe$^x$ or SLe$^x$-like construct and/or an SLe$^a$. or SLe$^a$-like construct. In some embodiments, the inhibitor of MPO enzymatic activity suitable for use in the methods of the present embodiments is an SLe$^x$ or SLe$^x$-like construct and/or an SLe$^a$. or SLe$^a$-like construct.

In some embodiments, the inhibitor of E-selectin receptor/MPO-EL interactions suitable for use in the methods of the present embodiments is a SLe$^x$ or SLe$^x$-like construct and/or an SLe$^a$. or SLe$^a$-like construct. In some embodiments, the inhibitor of MPO enzymatic activity suitable for use in the methods of the present embodiments is a SLe$^x$ or SLe$^x$-like construct and/or an SLe$^a$. or SLe$^a$-like construct.

The term "selectin" is employed to designate a general class of receptor which displays a selective adhesive function and which includes a lectin-like domain responsible for such selective adhesive function. E-selectin corresponds to glycoprotein ELAM-1 (endothelial leukocyte adhesion molecule-1).

Sialyl Lewis X (SLe$^x$) mediates binding of neutrophils to vascular endothelial cells by binding to E-selectin. (M. Phillips, et al., Science. 1990, 250, 1130; J. Lowe, et al, Cell. 1990, 63, 475; T. Feizi, Trends. Biochem. Sci. 1991, 16, 84; M. Tiemeyer., et al., Proc. Natl. Acad. Sci. U.S.A. 1991, 88, 1138; L. Lasky. Science. 1992, 258, 964; and T. Springer, L. A. Lasky, Nature 1991, 349, 196.) Sialyl Lewis X (SLe$^x$) is a cell surface carbohydrate ligand found on neutrophils, anchored onto the outer membrane thereof by integral membrane glycoproteins and/or glycolipids. Administration of SLe$^x$ inhibits the SLe$^x$/E-selectin interaction and blocks adhesion of neutophils to endothelial cells. (M. Buerke, et al., J. Clin. Invest., 1994, 1140.). Neutrophil-mediated inflammatory diseases may be treated by administration of Sialyl Lewis X (SLe$^x$). SLe$^x$ mimetics are disclosed in U.S. Pat. Nos. 5,830,871 and 5,858,994, incorporated herein by reference in their entireties. SLe$^a$ is an isomer of SLe$^x$ that also functions as a prototypical E-selectin binding glycan.

DeFrees et al., J. Am. Chem. Soc., 117:66-79 (1995) reported on the in vitro inhibition of binding between E-selectin and SLe$^x$-bearing HL-60 cells for a number of SLe$^x$-related materials including SLe$^x$ itself, an ethyl glycoside of the above pentamer and a number of bivalent SLe$^x$ analogs.

Two SLe$^x$ mimetics synthesized by Uchiyama et al. are of particular note because they exhibit activities similar to SLe$^x$ in the E-selectin binding assay. (T. Uchiyama, et al. J. Am. Chem. Soc. 1995, 117, 5395.) For active natural products inhibiting E-selectin, see Narasing a Rao, et al., J. Biol. Chem., 269:19663 (1994).

The key structural features of SLe$^x$ required for recognition by E-selectin have been determined by structural and conformational studies and by comparative studies of the blocking activity of SLe$^x$ analog families. (B. Brandley, Glycobiology 1993, 3, 633; S. DeFrees, J. Am. Chem. Soc. 1993, 115, 7549; J. Ramphal, J. Med. Chem. 1994, 37, 3459; D. Tyrrell, Proc. Natl. Acad. Sci. USA 1991, 88, 10372; R. Nelson, J. Clin. Invest. 1993, 91, 1157; and A. Giannis, Angew. Chem. Int. Ed. Engl. 1994. 33. 178.) The solution conformation of SLe$^x$ has been characterized using physical methodologies. (Y. C. Lin, et al., J. Am. Chem. Soc. 1992, 114, 5452; Y. Ichikawa, et al. J. Am. Chem. Soc., 1992, 114, 9283; and G. E. Ball et al., J. Am. Chem. Soc., 1992, 114, 5449.) The three-dimensional structure of the human E-selectin has been characterized by X-ray diffraction. (B. J. Graves, et al., Nature, 1994, 367, 532.) It has been found that the L-fucose, D-galactose (Gal) and sialic acid moieties of SLe$^x$ are the major components that interact with E-selectin. N-acetylglucosamine unit appears to act merely as a linker to connect L-fucose and sialyl galactose. The six functional groups of SLex molecule including the 2-, 3- and 4-OH groups of L-fucose, the 4- and 6-OH groups of Gal and the $—CO_2^-$ group of sialic acid are essential for E-selectin recognition.

Methods of Determining MPO Activity

MPO activity or inhibition of MPO activity may be determined by any of a variety of standard methods known in the art. See e.g., U.S. Publication No. 20110152224, U.S. Pat. No. 7,108,997, incorporated herein by reference in their entireties. One such method is a colorimetric-based assay where a chromophore that serves as a substrate for the peroxidase generates a product with a characteristic wavelength which may be followed by any of various spectroscopic methods including UV-visible or fluorescence detection. Additional details of colorimetric based assays can be found in Kettle, A. J. and Winterbourn, C. C. (1994) Methods in Enzymology. 233: 502-512; and Klebanoff, S. J., Waltersdorph, A. N. and Rosen, H. (1984) Methods in Enzymology. 105: 399-403, both of which are incorporated herein by reference. An article by Gerber, Claudia, E. et al, entitled "Phagocytic Activity and Oxidative Burst of Granulocytes in Persons with Myeloperoxidase Deficiency" published in 1996 in Eur. J. Clin. Chem Clin Biochem 34:901-908, describes a method for isolation for polymorphonuclear leukocytes (i.e. neutrophils) and measurement of myeloperoxidase activity with a colorimetric assay, which involves oxidation of the chromgen 4-chloro-1-naphthol.

Peroxidase activity may be determined by in situ peroxidase staining in MPO containing cells with flow cytometry-based methods. Such methods allow for high through-put screening for peroxidase activity determinations in leukocytes and subpopulations of leukocytes. An example is the cytochemical peroxidase staining used for generating white blood cell count and differentials with hematology analyzers based upon peroxidase staining methods. For example, the Advia 120 hematology system by Bayer analyzes whole blood by flow cytometry and performs peroxidase staining of white blood cells to obtain a total white blood cell count (CBC) and to differentiate amongst the various white blood cell groups.

With these methods, whole blood enters the instrument and red blood cells are lysed in a lysis chamber. The remaining white blood cells are then fixed and stained in situ for peroxidase activity. The stained cells are channeled into the flow cytometer for characterization based upon the intensity of peroxidase staining and the overall size of the cell, which is reflected in the amount of light scatter of a given cell. These two parameters are plotted on the x and y axis, respectively, by conventional flow cytometry software, and clusters of individual cell populations are readily discernible. These include, but are not limited, to neutrophils, monocytes and eosinophils, the three major leukocyte populations containing visible peroxidase staining.

During the course of these analyses, leukocytes such as monocytes, neutrophils, eosinophils and lymphocytes are identified by the intensity of peroxidase staining and their overall size. Information about the overall peroxidase activity staining within specific cell populations is thus inherent in the position of individual cell clusters (e.g. neutrophil, monocyte, eosinophil clusters) and peroxidase levels within specific cell populations may be determined. Peroxidase activity/staining in this detection method is compared to a peroxidase stain reference or calibrant. Individuals with higher levels of peroxidase activity per leukocyte are identified by having a cell population whose location on the cytogram indicates higher levels of peroxidase (i.e., average peroxidase activity per leukocyte) or by demonstrating a sub-population of cells within a cell cluster (e.g. neutrophil, monocyte, eosinophil clusters) which contain higher levels of peroxidase activity either on average or in a higher subgroup, such as the higher tertile or quartile.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. Thus, for example, a reference to "a hostcell" includes a plurality of such host cells, and a reference to "an antibody" is a reference to one or more antibodies and equivalents thereof known to those skilled in the art, and so forth.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

Particular embodiments of this invention embrace the use of inhibitory agents that selectively block the interaction or binding between an E-selectin receptor and an E-selectin ligand such as MPO or MPO-EL. As used herein, a "selective inhibitor of the E-selectin receptor and MPO-EL interaction" or "an agent that selectively inhibits the interaction between E-selectin receptor and MPO-EL" is any molecular species that is an inhibitor of the binding between E-selectin receptor and MPO-EL, but which fails to inhibit, or inhibits to a substantially lesser degree, the interaction between E-selectin receptor and other E-selectin ligands.

As used herein, the term "myeloperoxidase" or "MPO" refers to a protein that comprises the full-length myeloperoxidase for given species (e.g. human). The term "myeloperoxidase" or "MPO" encompasses the novel glycoform disclosed herein, MPO-EL. The preferred MPO species is human MPO or human MPO-EL.

As used herein, the term "myeloperoxidase activity" refers to the turnover or consumption of a substrate based on a quantifiable amount (e.g., mass) of a MPO. In other words, MPO activity refers to the amount of MPO needed to convert or change a substrate into the requisite product in a given time. Methods for determining or quantifying myeloperoxidase activity are well known in the art. For example, one method that could be used to determine myeloperoxidase activity is an immunoassay (such as, for example, affinity chromatography, immunoelectrophoresis, radioimmunoassay (RIA), enzyme-linked immunosorbent assays (ELISAs), immunofluorescent assays, Western blotting, and the like).

Such immunoassays can be homogeneous or heterogeneous immunoassays. Alternatively, MPO activity can be determined using a chemiluminescent assay such as that described in U.S. Publication No. 20090053747, the contents of which are herein incorporated by reference. Still another method that can be used to determine MPO activity is a colorimetric-based assay where a chromophore that serves as a substrate for the peroxidase generates a product with a characteristic wavelength which may be followed by any of various spectroscopic methods including UV-visible or fluorescence detection such as that described in U.S. Pat. No. 7,223,552, the contents of which are also incorporated by reference in their entirety.

Leukocytosis is a raised white blood cell count (the leukocyte count) above the normal range in the blood. It is frequently a sign of an inflammatory response. There are five principle types of leukocytosis: Neutrophilia (the most common form); Lymphocytosis; Monocytosis; Eosinophilia; and Basophilia. A leukocyte count above 25 to $30 \times 10^9/L$ is termed a leukemoid reaction, which is the reaction of a healthy bone marrow to extreme stress, trauma, or infection. It is different from leukemia and from leukoerythroblastosis, in which either immature white blood cells (acute leukemia) or mature, yet non-functional, white blood cells (chronic leukemia) are present in peripheral blood.

Acute myocardial infarction (AMI) refers to a blockage of one or more of the coronary arteries. Coronary arterial occlusion due to thrombosis is the cause of most cases of AMI. This blockage restricts the blood supply to the muscle walls of the heart and is often accompanied by symptoms such as chest pain, heavy pressure in the chest, nausea, and shortness of breath, or shooting pain in the left arm. AMI is accompanied with an inflammatory reaction which induces cardiac dysfunction and scarring. Rapid restoration of blood flow to jeopardized myocardium limits necrosis and reduces mortality.

"Restenosis" refers to the renewed narrowing of an artery, e.g. a coronary artery, following a vessel opening or widening procedure, such as angioplasty or atherectomy. In restenosis, a vessel that has been treated to at least minimize the volume of a lesion or blockage and thereby restore blood flow, e.g. by balloon angioplasty, starts to renarrow, typically within about six months of the vessel widening procedure. This renarrowing often requires additional treatment, such as additional angioplasty procedures. It has been estimated that as much as one third to one half of all angioplasty procedures are followed by restenosis within the first six months to one year following the initial vessel widening procedure.

In some embodiments, MPO or MPO-EL of the present embodiments comprises the amino acid sequence of SEQ ID NO: 1, SEQ ID NO: 2, or SEQ ID NO: 3. In some embodiments, MPO of the present embodiments comprises an amino acid sequence that is 80% identical to any one of SEQ ID NO: 1, SEQ ID NO: 2, or SEQ ID NO: 3.

In some embodiments, MPO or MPO-EL of the present embodiments comprises an amino acid sequence that is 90% identical to any one of SEQ ID NO: 1, SEQ ID NO: 2, or SEQ ID NO: 3. In some embodiments, MPO or MPO-EL of the present embodiments comprises an amino acid sequence that is 95% identical to any one of SEQ ID NO: 1, SEQ ID NO: 2, or SEQ ID NO: 3.

```
SEQ ID NO: 1 is as follows:
MGVPFFSSLRCMVDLGPCWAGGLTAEMKLLLALAGLLAILATPQPSEGAAPAVLGEVDTSLVLSSM
EEAKQLVDKAYKERRESIKQRLRSGSASPMELLSYFKQPVAATRTAVRAADYLHVALDLLERKLRS
LWRRPFNVTDVLTPAQLNVLSKSSGCAYQDVGVTCPEQDKYRTITGMCNNRRSPTLGASNRAFVRW
LPAEYEDGFSLPYGWTPGVKRNGFPVALARAVSNEIVRFPTDQLTPDQERSLMFMQWGQLLDHDLD
FTPEPAARASFVTGVNCETSCVQQPPCFPLKIPPNDPRIKNQADCIPFFRSCPACPGSNITIRNQI
NALTSFVDASMVYGSEEPLARNLRNMSNQLGLLAVNQRFQDNGRALLPFDNLHDDPCLLTNRSARI
PCFLAGDTRSSEMPELTSMHTLLLREHNRLATELKSLNPRWDGERLYQEARKIVGAMVQIITYRDY
LPLVLGPTAMRKYLPTYRSYNDSVDPRIANVFTNAFRYGHTLIQPFMFRLDNRYQPMEPNPRVLPL
SRVFFASWRVVLEGGIDPILRGLMATPAKLNRQNQIAVDEIRERLFEQVMRIGLDLPALNMQRSRD
HGLPGYNAWRRFCGLPQPETVGQLGTVLRNLKLARKLMEQYGTPNNIDIWMGGVSEPLKRKGRVPG
LLACIIGTQFRKLRDGDRFWWENEGVFSMQQRQALAQISLPRIICDNTGITTVSKNNIFMSNSYPR
DFVNCSTLPALNLASWREAS SEQ ID NO: 2 is as follows:
MGVPFFSSLRCMVDLGPCWAGGLTAEMKLLLALAGLLAILATPQPSEGAAPAVLGEVDTSLVLSS
MEEAKQLVDKAYKERRESIKQRLRSGSASPMELLSYFKQPVAATRTAVRAADYLHVALDLLERKLR
SLWRRPFNVTDVLTPAQLNVLSKSSGCAYQDVGVTCPEQDKYRTITGMCNNRRSPTLGASNRAFVR
WLPAEYEDGFSLPYGWTPGVKRNGFPVALARAVSNEIVRFPTDQLTPDQERSLMFMQWGQLLDHDL
DFTPEPAARASFVTGVNCETSCVQQPPCFPLKIPPNDPRIKNQADCIPFFRSCPACPGSNITIRNQ
INALTSFVDASMVYGSEEPLARNLRNMSNQLGLLAVNQRFQDNGRALLPFDNLHDDPCLLTNRSAR
IPCFLAGDTRSSEMPELTSMHTLLLREHNRLATELKSLNPRWDGERLYQEARKIVGAMVQIITYRD
YLPLVLGPTAMRKYLPTYRSYNDSVDPRIANVFTNAFRYGHTLIQPFMFRLDNRYQPMEPNPRVPL
SRVFFASWRVVLEGGIDPILRGLMATPAKLNRQNQIAVDEIRERLFEQVMRIGLDLPALNMQRSRD
HGLPGYNAWRRFCGLPQPETVGQLGTVLRNLKLARKLMEQYGTPNNIDIWMGGVSEPLKRKGRVGP
LLACIIGTQFRKLRDGDRFWWENEGVFSMQQRQALAQISLPRIICDNTGITTVSKNNIFMSNSYPR
DFVNCSTLPALNLASWREAS SEQ ID NO: 3 is as follows:
MRLLLGLAGLLAVLIMLQPSEGVPPAVPGEVDTSVVLTCMEEAKRLVDKVYKERRESIKQRLHSGL
ASPMELLSYFKQPVAATRTAVRAADYLHVALSLLERKLRALWPGRFNVTDVLTPAQLNLLSKTSGC
AHQDLGVSCPEKDEYRTITGQCNNRRSPTLGASNRPFVRWLPAEYEDGFSLPFGWTPRVKRNGFPV
PLARAVSNEIVRFPTEKLTPDQQRSLMFMQWGQLLDHDLDFSPEPAARVSFLTGINCETSCLQQPP
CFPLKIPPNDPRIKNQQDCIPFFRSSPACTQSNITIRNQINALTSFVDASMVYGSEDPLAMRLRNL
TNQLGLLAVNTRFQDNGRALLPFDTLRHDPVRLTNRSANIPCFLAGDSRASEMPELTSMHTLFVRE
HNRLAKELKRLNAHWNGERLYQEARKIVGAMVQIITYRDYLPLVLGREAMRKYLRPYCSYNDSVDP
RISNVFTNAFRYGHTLIQPFMFRLNSRYQPMQPNPRVPLSRVFFASWRVVLEGGISPILRGLMATP
AKLNRQNQIAVDEIRERLFEQVMRIGLDLPALNMQRSRDHGLPGYNAWRRFCGLPVPNTVGELGTV
LRNLDLARRLMKLYQTPNNIDIWIGGVAEPLNKNGRVGPLLACIIGTQFRKLRDGDRFWWQNKGVF
SKKQQQALAKISLPRIICDNTGITFVSKNNIFMSNRFPRDFVRCSRVPALNLAPWRERR
```

EXAMPLES

It is understood that modifications which do not substantially affect the activity of the various embodiments of this invention are also provided within the definition of the invention provided herein. Accordingly, the following examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

Example 1

G-CSF Induces a Pleiotropic Glycovariant of Myeloperoxidase

The results summarized in this example provide the first evidence for functional pleiotropism of myeloperoxidase (MPO), a well-characterized lysosomal enzyme best known for generation of cytotoxic oxidants. Specifically, it is shown that G-CSF induces expression of a cell surface glycoform of MPO that serves as an E-selectin ligand (MPO-E-selectin Ligand, "MPO-EL"), and that this molecule is an effector of both leukocyte-endothelial adhesion and angiotoxicity.

G-CSF-treated human myeloid cells induce E-selectin-dependent cytotoxicity in cultured endothelial cells and depression of cardiac function in a mouse myocardial infarct model. G-CSF promotes expression of E-selectin ligands on human myeloid cells, including an uncharacterized ~65 kDa glycoprotein. Biochemical studies show that this novel E-selectin ligand is a catalytically active, sialofucosylated glycoform of myeloperoxidase (MPO), a well-known lysosomal enzyme. This specialized MPO glycoform is expressed on circulating G-CSF-mobilized leukocytes, and is inducible on blood leukocytes and marrow-derived myeloid cells by G-CSF treatment. Inhibition of MPO activity abrogates E-selectin-dependent endothelial injury. Disruption of complex N-linked glycan biosynthesis prevents G-CSF-induced MPO membrane expression and, concomitantly, blunts angiotoxicity. These findings define a unique E-selectin ligand and unveil previously unsuspected MPO functional pleiotropism, placing this lysosomal enzyme at the nexus of leukocyte migration and vascular pathology.

Administration of human G-CSF-mobilized leukocytes (ML), but not human native leukocytes (NL), worsens cardiac function in mice with surgically induced myocardial infarct. Moreover, co-incubation of cytokine-stimulated human umbilical vein endothelial cells (HUVEC) with ML induced robust angiotoxicity that was abrogated by disruption of E-selectin receptor/ligand interactions. These findings prompted us to identify the ~65 kDa E-selectin ligand specific to G-CSF-mobilized myeloid cells, and to examine its role(s) in vasculopathy. Biochemical and mass spectrometry studies reveal that this membrane molecule comprises the heavy chain of a unique glycovariant of MPO, designated "MPO-EL-selectin Ligand" (MPO-EL or MPO-EL). We identified that G-CSF treatment of myeloid cells induces surface MPO expression, concomitant with the elaboration of specialized N-linked glycan determinants rendering E-selectin ligand activity. MPO-EL is catalytically active on the cell membrane and MPO inhibition abrogates myeloid cell cytotoxicity to vascular endothelium. Heretofore, a leukocyte surface molecule mediating both leukocyte trafficking and cytotoxicity has not been identified. Our findings thus reveal previously unrecognized biologic pleiotropism of both E-selectin ligands and of MPO, yielding unifying perspectives on the well-known association between G-CSF administration and vascular complications and between MPO and vascular inflammatory conditions.

Results

Intravascular administration of human ml accentuates cardiac injury in mice following surgically-induced myocardial infarct. Administration of G-CSF to patients with acute myocardial infarct is associated with coronary restenosis and cardiac depression, and, in patients with coronary artery disease, G-CSF administration can induce angina pectoris and myocardial infarct. To directly assess whether human G-CSF-mobilized leukocytes impact cardiac function following ischemic insult, we administered PBS (control) and human NL and ML to mice (via jugular vein infusion) within five hours of surgically-induced myocardial infarct. Echocardiograms performed three days after infarct showed "stunned" myocardium, with equivalently dampened cardiac function in all treatment groups (FIG. 1a) However, compared to day 3 values, echocardiograms at 7 days post-infarct showed marked improvement in ejection fraction in mice receiving PBS and NL, whereas mice injected with ML had sustained profound depression of ejection fraction (FIG. 1a). These results indicate that administration of G-CSF-primed leukocytes contributed to significant, irreversible cardiac injury following myocardial ischemia.

Figure 1B:
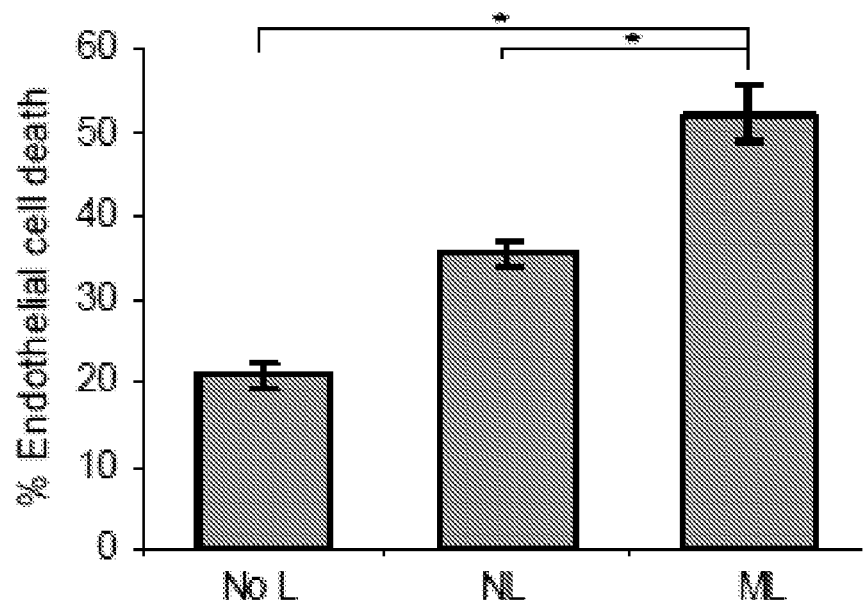

Assessment of angiotoxicity of NL and ML. Based on the observed effects of human ML administration in the mouse myocardial injury model, we sought to determine whether ML alters the integrity of inflamed endothelium. Accordingly, we incubated primary human umbilical vein endothelial cells (HUVEC) with TNF-α to induce endothelial activation. Stimulated HUVEC were then incubated in absence of leukocytes, or with addition of NL or ML. Endothelial cell viability was monitored by trypan blue exclusion. As shown in FIG. 1 b, there was baseline endothelial cell death after 48 h in TNF-α-stimulated HUVEC cultures without leukocyte (No L). Incubation of TNF-α-stimulated HUVEC with NL increased endothelial cell death above baseline, and angiotoxicity was profoundly enhanced by incubation with ML (FIG. 1 b).

Disruption of e-selectin receptor/ligand interactions blunts angiotoxicity of ml. Because we had previously observed that G-CSF induces E-selectin ligand expression on human myeloid cells, we analyzed whether angiotoxicity observed in co-culture of stimulated HUVEC with leukocytes was dependent on E-selectin binding. To this end, TNF-α-stimulated HUVEC were incubated with NL, with bone marrow-derived cells ("BM", comprised predominantly of myeloid progenitor cells), or with ML in the presence or absence of function-blocking anti-E-selectin mAb. As shown in FIG. 1c, incubation of HUVEC with NL and BM cells induced endothelial cell death, and treatment of HUVEC with function-blocking anti-E-selectin mAb had no effect on baseline endothelial cell death (i.e., in absence of leukocytes), nor on angiotoxicity induced by NL and BM cells. However, the striking increase in endothelial death observed in co-culture of ML was dramatically reduced by treatment with anti-E-selectin mAb, to levels observed in co-culture with NL and BM cells. Altogether, these findings indicate that in vivo G-CSF treatment heightens myeloid cell angiotoxicity that is critically dependent on E-selectin receptor/ligand interactions.

Figures 2A, 2B, 2C:
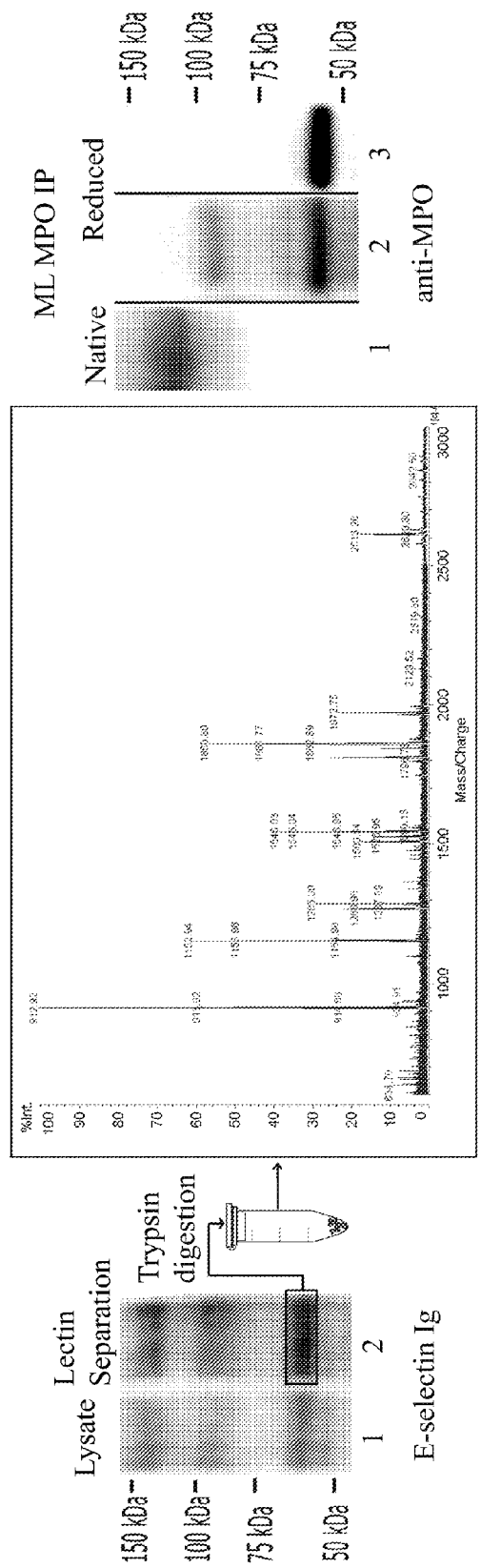
FIGS. 2 A-C. Identification of the ~65 kDa E-selectin ligand. (A) Representative results of lysates of ML (Lane 1) and WGA lectin chromatography-purified glycoproteins (Lane 2) resolved in parallel on reducing 7.5% SDS-PAGE gel and immunoblotted with E-selectin-Ig chimera. As shown in Lane 1, E-selectin ligands are present at ~140 kDa (PSGL-1), ~100 kDa (HCELL) and at ~65 kDa, each of which are preserved and concentrated after lectin chromatography (Lane 2). (B) In-gel trypsin digestion and mass spectrometry (MS) analysis of ~65 kDa lectin-purified glycoprotein. MPO (MS profile shown) was identified as the main protein. (C) Representative results of western blots of MPO immunoprecipitates (IP) from ML resolved under non-reducing (Lane 1) or reducing conditions (Lanes 2 and 3) and stained with anti-MPO mAb. In non-reduced gels, the mature homodimer of ~140 kDa is evident (Lane 1). Under reducing conditions, western blot with anti-MPO mAb 2C7 (Lane 2) reveals bands at ~90 kDa (precursor) and ~65 kDa (heavy chain), or only the ~65 kDa band when stained with anti-MPO mAb 3D3 (Lane 3).

Identification of the ~65 kDa E-selectin ligand induced by G-CSF. ML display the E-selectin ligands CLA and HCELL, and an uncharacterized E-selectin ligand glycoprotein of ~65 kDa. Since CLA and HCELL are expressed on immature bone marrow myeloid cells, and on NL, we reasoned that the enhanced E-selectin-dependent angiotoxicity observed in ML might be mediated by the novel ~65 kDa ligand. To identify this structure, ML proteins were separated over wheat germ agglutinin (WGA) lectin columns. The glycoprotein fraction was collected, resolved by SDS-PAGE, and E-selectin ligands were detected by staining with E-selectin-Ig chimera (E-Ig). As shown in parallel gel lanes normalized for input protein content, the WGA chromatography step preserved and concentrated E-selectin ligands present in ML lysates (Lanes 1 and 2, FIG. 2a). A series of gel bands were then excised from the 60-70 kDa region, digested with trypsin and subjected to MALDI mass spectrometry. In repeated preparations, peptide mass fingerprinting coupled with bioinformatics analysis identified the ~65 kDa protein as the heavy chain of MPO (FIG. 2b). To confirm the identity of the ~65 kDa molecule, MPO was immunoprecipitated (IP) from ML lysates and resolved by SDS-PAGE under non-reducing or reducing conditions. Western blotting with anti-MPO mAb revealed only the ~130-140 kDa homodimer under non-reducing conditions (FIG. 2c Lane 1). Under reducing conditions, the precursor at ~90 kDa and the heavy chain at ~65 kDa were stained using anti-MPO mAb 2C7 (FIG. 2c Lane 2), while the heavy chain was predominantly stained using anti-MPO mAb 3D3 (FIG. 2c Lane 3).

Figure 3A:
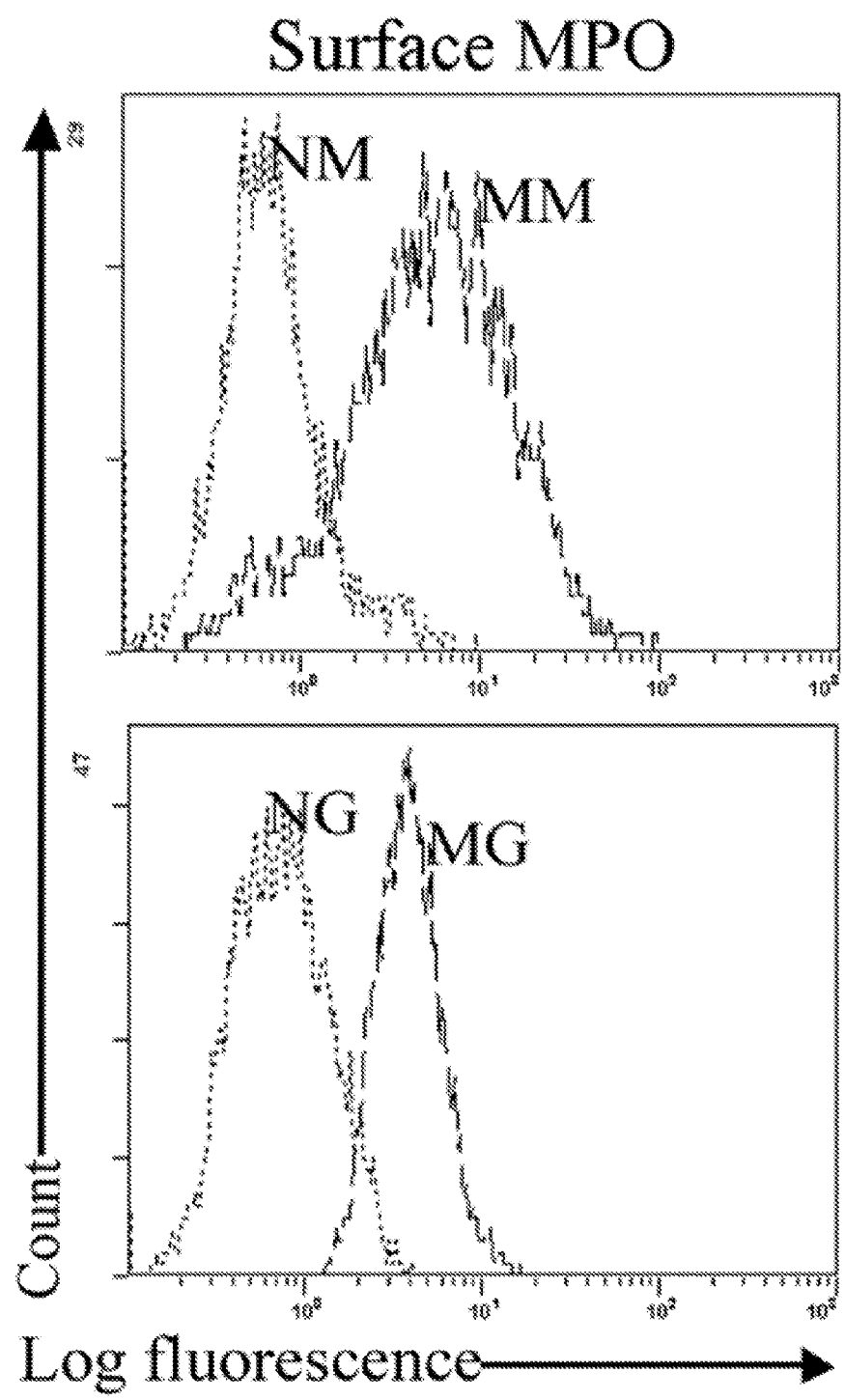
FIGS. 3 A-D. Catalytically active MPO is expressed on the cell surface of G-CSF mobilized leukocytes. Membrane expression of MPO was monitored in subsets of native or G-CSF mobilized leukocytes. (A) Representative MPO flow cytometry histograms are shown of native granulocytes (NG) and native mononuclear cells (NM) in comparison to mobilized granulocytes (MG) and mobilized mononuclear cells (MM). (B) Cumulative results of flow cytometry analysis for MPO cell surface expression typical for mononuclear cells and granulocytes. Values represent mean±SD of percent positive cells from multiple donors (n=15), *p<0.001. (C) Representative western blot of MPO immunoprecipitates (mAb 2C7) of lysates of surface biotinylated (+) or non-biotinylated (−) ML and NL resolved on reducing SDS-PAGE gel. Biotin-labeled (membrane expressed) MPO was revealed with Streptavidin-HRP. (D) MPO activity on the surface of NL and ML was evaluated by spectrophotometric detection of OPD, a chromogenic peroxidase product (n=5 donors of NL or ML).
Figure 3B:
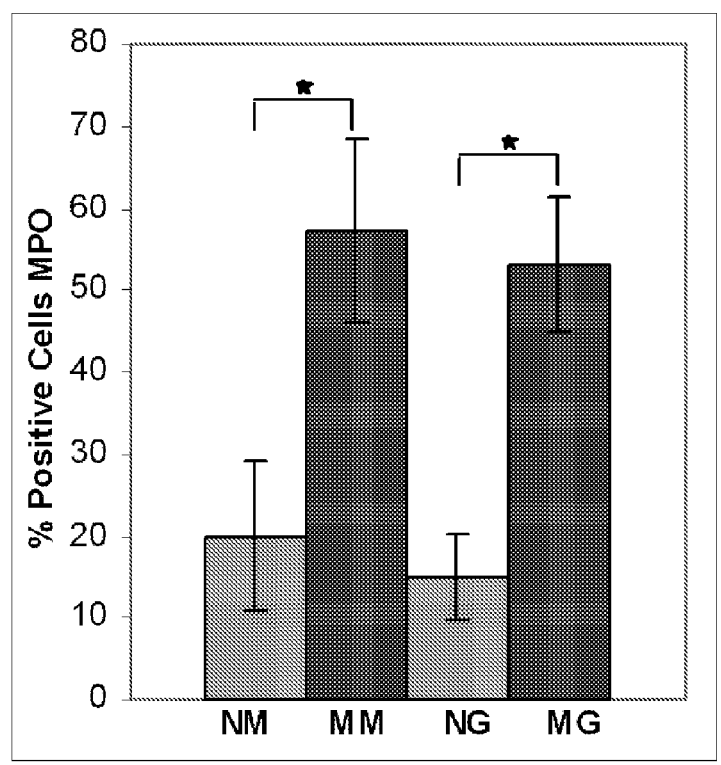
Figure 3C:
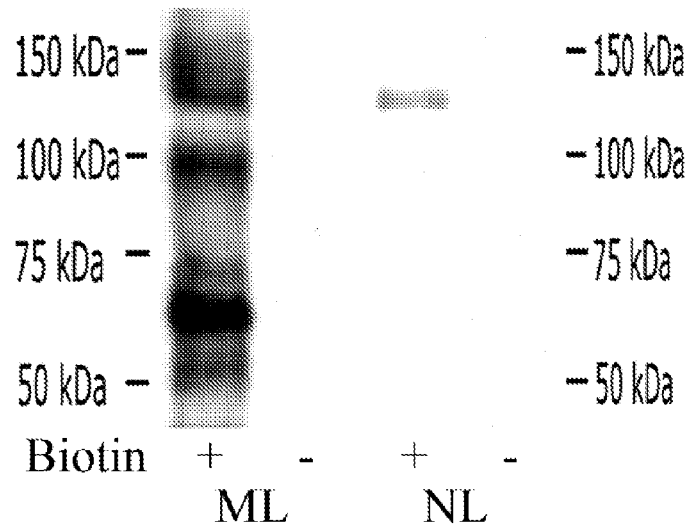
Figure 3D:
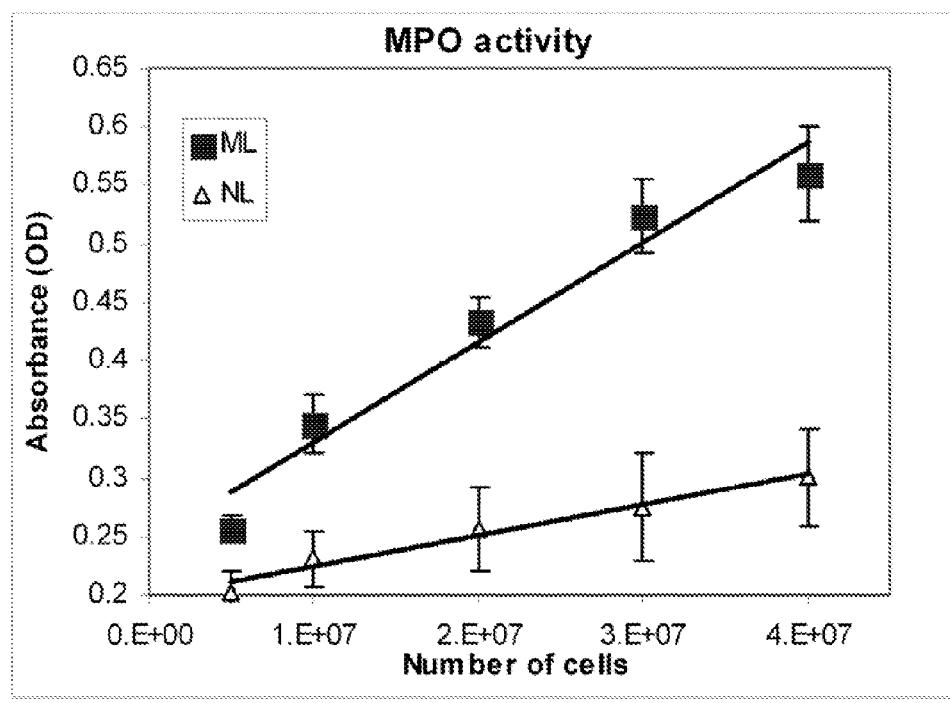

Analysis of cell surface expression of MPO on ML and NL. MPO is characteristically stored in native leukocytes within azurophilic granules. To assess surface expression of MPO on NL and ML, granulocyte and monocyte fractions from each leukocyte type were analyzed by flow cytometry. As shown in FIGS. 3a and 3b, NL granulocytes (NG) and monocytes (NM) express minimal surface MPO, whereas mobilized granulocytes (MG) and monocytes (MM) display uniformly high levels of membrane MPO (FIGS. 3a, 3b). To confirm MPO surface expression, a complementary approach was undertaken whereby cell membrane proteins from freshly collected NL and ML were labeled with biotin. MPO immunoprecipitates from lysates of surface biotinylated cells were resolved by electrophoresis and blotted with streptavidin-HRP. The western blots revealed biotinylated MPO prominently in ML, whereas NL showed only trace amounts on the cell surface (FIG. 3c). Extensive cell washes under high salt conditions (1.5 M NaCl) did not alter ML surface MPO levels, nor did digestion of glycosylphosphatidylinisotol (GPI) anchors with phosphatidylinositol-specific phospholipase C (PI-PLC; enzyme effectiveness confirmed by loss of CD55, as measured by flow cytometry), indicating that MPO is an integral membrane component (data not shown). To determine the activity of surface MPO, ML membrane proteins labeled with biotin were captured with streptavidin-conjugated beads and incubated with a peroxidase substrate. Spectrophotometric analysis revealed a linear correlation between MPO activity and input cell number (FIG. 3d). Collectively, these results indicate that in vivo G-CSF treatment markedly up-regulates expression of catalytically-active MPO on the surface of mobilized myeloid cells.

In Vivo G-CSF administration induces expression of MPO-EL, an E-selectin binding glycoform of MPO. E-selectin ligand glycoproteins display sialofucosylated epitopes reactive with mAb HECA-452. To directly assess whether MPO serves as an E-selectin ligand, MPO was immunoprecipitated from lysates of NL and ML, resolved by SDS-PAGE, and blotted with E-Ig. As shown in FIG. 4a, in immunoprecipitation of lysates normalized for input cell numbers, MPO from ML showed dramatically more E-selectin ligand activity than that of NL. Specificity of E-selectin ligand activity was confirmed by abrogation of E-Ig staining in the presence of EDTA and by treating immunoprecipitates with sialidase (data not shown). To determine whether the observed differences in E-Ig reactivity were resultant from variations in MPO levels, MPO was immunoprecipitated from equivalent cell numbers of BM, NL and ML, resolved on SDS-PAGE and blotted with an anti-MPO Ab which predominantly recognizes the heavy chain (clone 3D3) (FIG. 4b). The blots were then stripped and stained with E-Ig (FIG. 4c). As shown in FIGS. 4b and 4c, though there was little variation in MPO staining among the samples, MPO from ML displayed markedly more E-Ig reactivity than that of BM or NL.

Figure 4D:
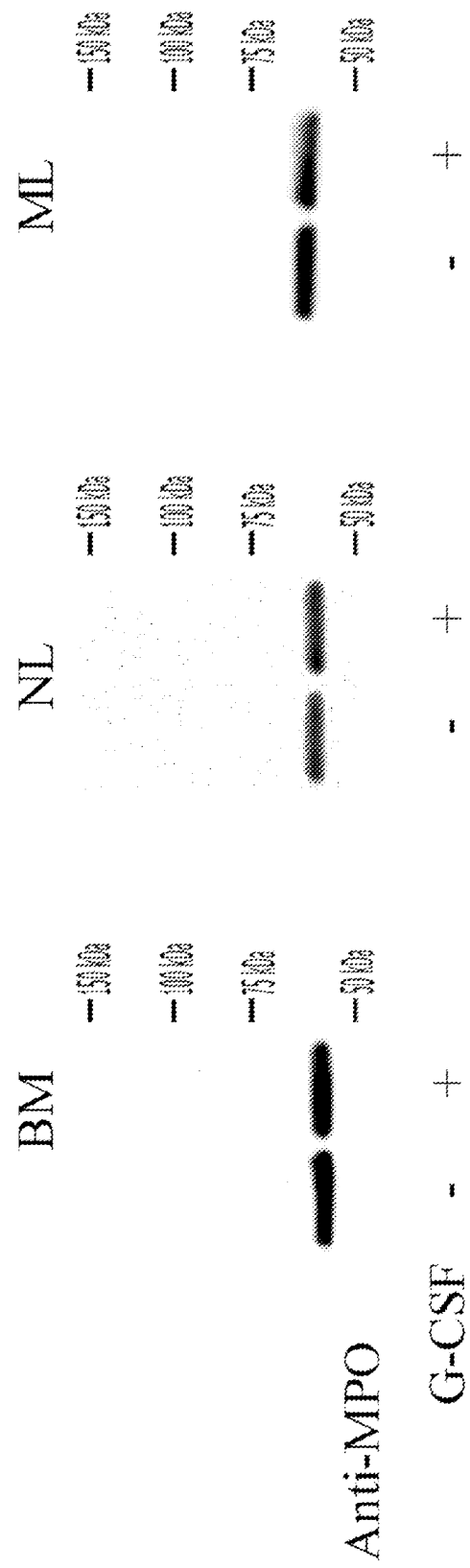
FIGS. 4 A-E. G-CSF induces expression of MPO-EL, an E-selectin binding glycoform of MPO. Representative blots of lysates of NL and ML are shown. (A) MPO immunoprecipitates (IPs; mAb 3D3) resolved on reducing SDS-PAGE and stained with E-selectin Ig chimera. (B) MPO IPs from lysates of BM, NL and ML stained in western blot with anti-MPO Ab 3D3. (C) Western blot of membrane in (B) stripped and probed with E-selectin Ig. (D) MPO IPs from BM, NL and ML treated (+) or not treated (−) with G-CSF and stained with anti-MPO mAb 3D3. (E) Western blot of membrane in (D) stripped and probed with E-selectin Ig.
Figure 4E:
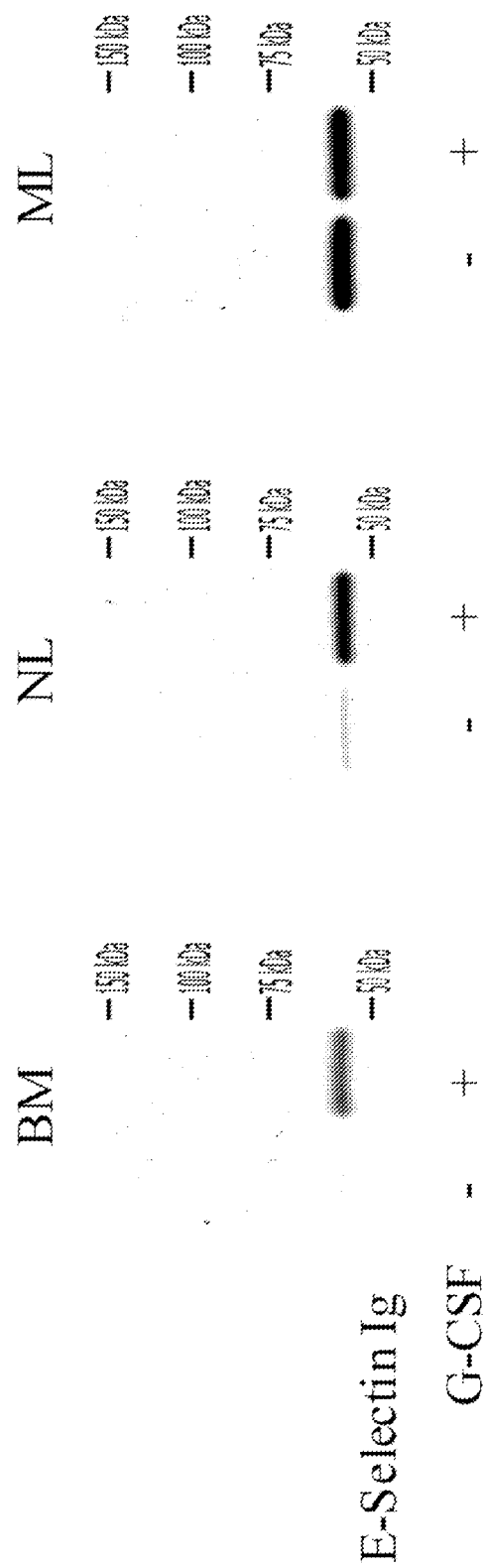

G-CSF induces MPO-EL expression in myeloid cells in vitro. To directly assess whether G-CSF stimulates expression of MPO-EL, freshly obtained BM, NL and ML were placed in culture and treated for 48 hours with human G-CSF at 10 ng/ml, a dose reflecting physiologic concentrations of G-CSF following in vivo administration[21,37]. MPO was immunoprecipitated from equivalent cell numbers of BM, NL and ML, then resolved on SDS-PAGE and blotted with an anti-MPO Ab which predominantly recognizes the heavy chain (clone 3D3) (FIG. 4d); blots were then stripped and stained with E-Ig (FIG. 4e). As shown in FIG. 4e, G-CSF markedly induces MPO-EL expression in both BM and NL, without significant increase in MPO quantity (FIG. 4d). Notably, ex vivo exposure to G-CSF did not further increase MPO-EL expression in ML (FIG. 4d). These results provide direct evidence that G-CSF induces MPO-EL expression on human myeloid cells.

Figure 5B:
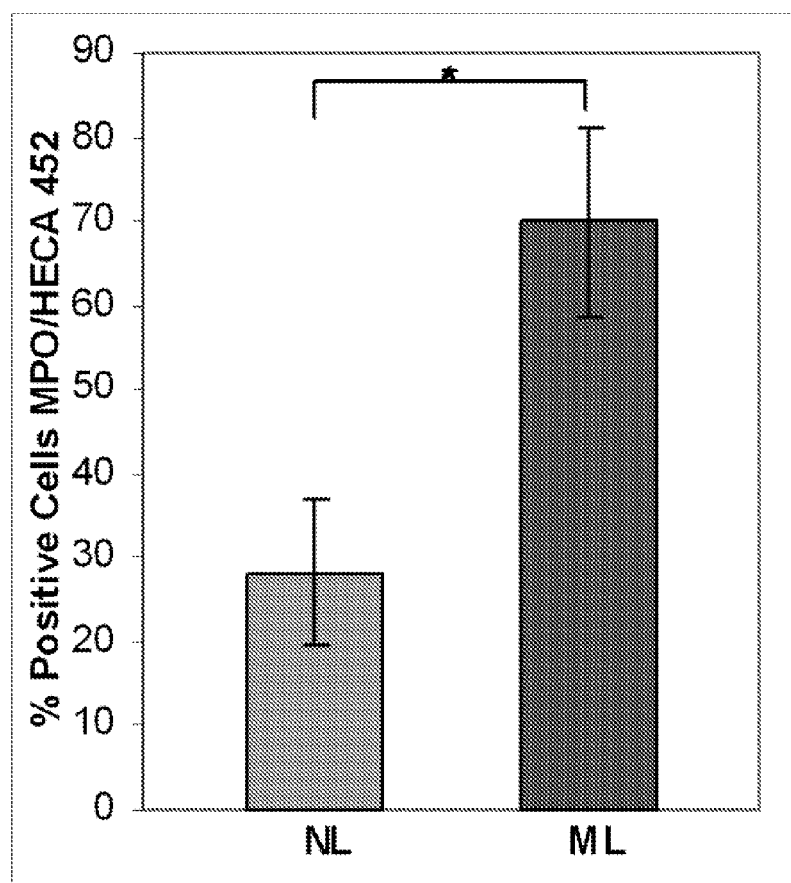
FIGS. 5 A-H. N-glycan processing is required for G-CSF induced surface MPO expression and HECA-452 reactivity. (A) Representative flow cytometry plots of NL and ML double-stained with FITC-conjugated HECA-452 and PE-conjugated anti-MPO mAb. (B) Cumulative flow cytometry results of NL and ML co-stained with HECA-452 and anti-MPO mAb. Values represent mean±SD of percent positive cells from multiple donors (n=12), *p<0.001. (C and D) Flow cytometry analysis of NL, BM and ML cultured for 48 h without G-CSF (−) or with G-CSF (+): (C) Anti-MPO mAb membrane staining, values represent mean±SD of percent positive cells from multiple donors (n>30), *p<0.001; (D) HECA-452 staining, values represent mean±SD of mean channel fluorescence of cells from multiple donors (n>30), *p<0.01. (E and F) Flow cytometry analysis of BM cells treated with neuraminidase and cultured with G-CSF or G-CSF and DMJ: (E) HECA-452 ligand expression and (F) MPO expression. (E, F panel 1) BM treated with neuraminidase and cultured for 48 h (+NA after 48 h) or buffer alone (−NA after 48 h). (E panel 1) Neuraminidase efficiency was confirmed before cell culturing (+NA after 1 h). (E, F panel 2) BM cells treated with neuraminidase and cultured for 48 h without G-CSF (+NA after 48 h) or with G-CSF (+NA+G-CSF after 48 h). (E, F panel 3) BM cells treated with neuraminidase and cultured for 48 h with G-CSF (+NA+G-CSF after 48 h) or with GCSF and DMJ (+NA+G-CSF+DMJ after 48 h). (G) Spectrophotometric detection of membrane MPO activity from NL cultured in the presence or absence of G-CSF and DMJ. Values represent the relative change in absorbance with respect to substrate alone (n=5), *p<0.001. (H) Endothelial cell death was evaluated after co-culture with NL treated with or without G-CSF and DMJ. Values represent mean±SD of percent endothelial cell death (n=5), *p<0.05.

G-CSF induces MPO-EL expression via N-glycan-dependent decoration of MPO with HECA-452-reactive, sialofucosylated determinants. Consistent with our prior results[21], flow cytometry showed that both NL and ML are decorated with HECA-452-reactive glycans, but ML display markedly increased HECA-452 reactivity compared to NL (data not shown). To assess HECA-452 expression relative to surface MPO levels on NL and ML, dual cell surface staining with HECA-452 and anti-MPO mAb was performed. As shown in FIG. 5a, there was increased expression, in percent marker-positive cells and mean channel fluorescence, of both surface MPO and HECA-452-reactive glycans in ML compared to NL. Cumulative results (n=15 for NL and ML) for dual marker co-expression are shown in FIG. 5b.

To directly examine the effect(s) of G-CSF on cell surface expression of MPO and HECA-452-reactive sialofucosylations, NL, BM and ML were treated ex vivo with G-CSF. Changes in membrane expression of sialofucosylated glycans and MPO were measured by cell surface staining with HECA-452 and anti-MPO mAb, respectively. G-CSF treatment of NL and BM cells dramatically increased expression of surface MPO (FIG. 5c), but, in contrast, ex vivo G-CSF treatment only modestly increased MPO membrane expression in ML (FIG. 5c). Flow cytometry analysis showed a significant increase of HECA452-reactive glycans on NL and BM after G-CSF administration and only modest increases on ML cells (FIG. 5d).

Figure 5E:
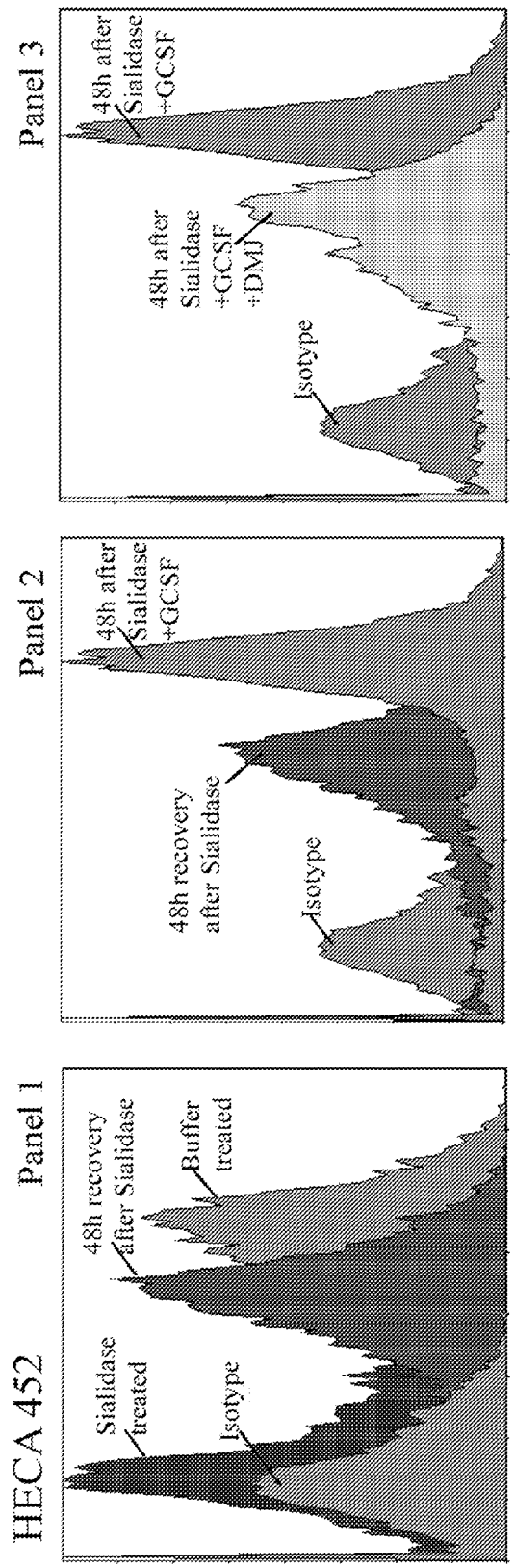
Figure 5F:
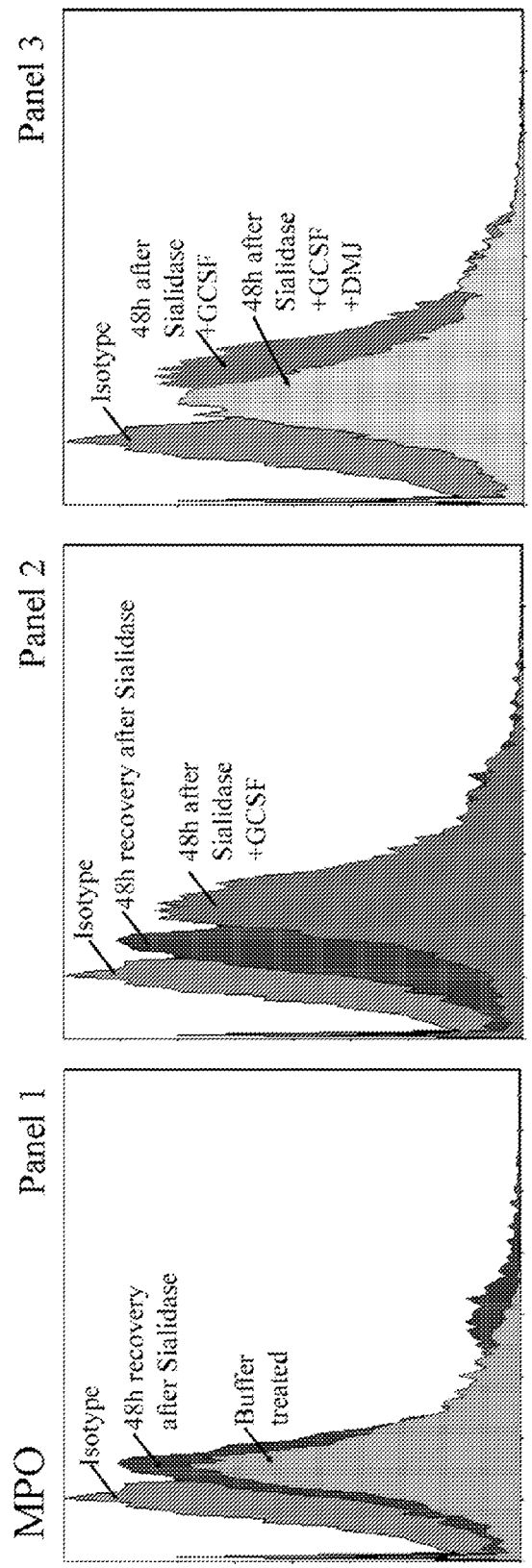

Glycoproteins bearing high mannose N-glycans, such as typically found on lysosomal MPO, require glycosidase-remodeling to display sialofucosylated determinants on lactosamine scaffolds. To assess whether such glycan processing is prerequisite for cell membrane expression of MPO, we employed deoxymannojirimycin (DMJ), an α-mannosidase inhibitor that hinders remodeling of high mannose N-glycans into complex carbohydrates. To this end, BM cells were treated with neuraminidase (NA) to eliminate existing E-selectin binding determinants or treated with buffer alone. Thereafter, cells were cultured with or without G-CSF in the presence or absence of DMJ to analyze de novo expression of HECA-452 determinants and of membrane MPO. After 48 h, in the absence of G-CSF and DMJ, NA-treated IBM cells recovered expression of HECA-452-reactive glycans to a level approximating that of buffer treated cells (FIG. 5e, panel 1). Importantly, cells treated with NA followed by incubation with G-CSF showed marked increased expression of HECA-452 determinants compared with cells not treated with G-CSF, whereas cells cultured with G-CSF in the presence of DMJ markedly diminished the G-CSF-induced expression of HECA-452-reactive glycans, to levels seen in recovery in the absence of G-CSF (FIG. 5e, compare panels 2 and 3). These findings suggest that G-CSF stimulates de novo expression of HECA-452-reactive moieties predominantly on N-glycans. The residual HECA-452-determinants displayed in the presence of DMJ likely reflect the native contribution(s) of sialofucosylated O-linked glycans found on both glycoproteins and glycolipids. Treatment of cells with NA did not induce MPO expression (FIG. 5f, panel 1), nor did pretreatment with NA alter the G-CSF-induced expression of membrane MPO (FIG. 5f, panel 2). However, G-CSF-induced MPO expression was significantly attenuated in the presence of DMJ, to levels equivalent to that of cells not treated with G-CSF (FIG. 5f, panel 3). G-CSF induces expression of Golgi glycosyltransferases that synthesize sialofucosylated glycans, showing that surface expression of MPO-EL is dependent on G-CSF-induced remodeling of MPO N-glycans into complex sialofucosylated carbohydrates.

Figure 5G:
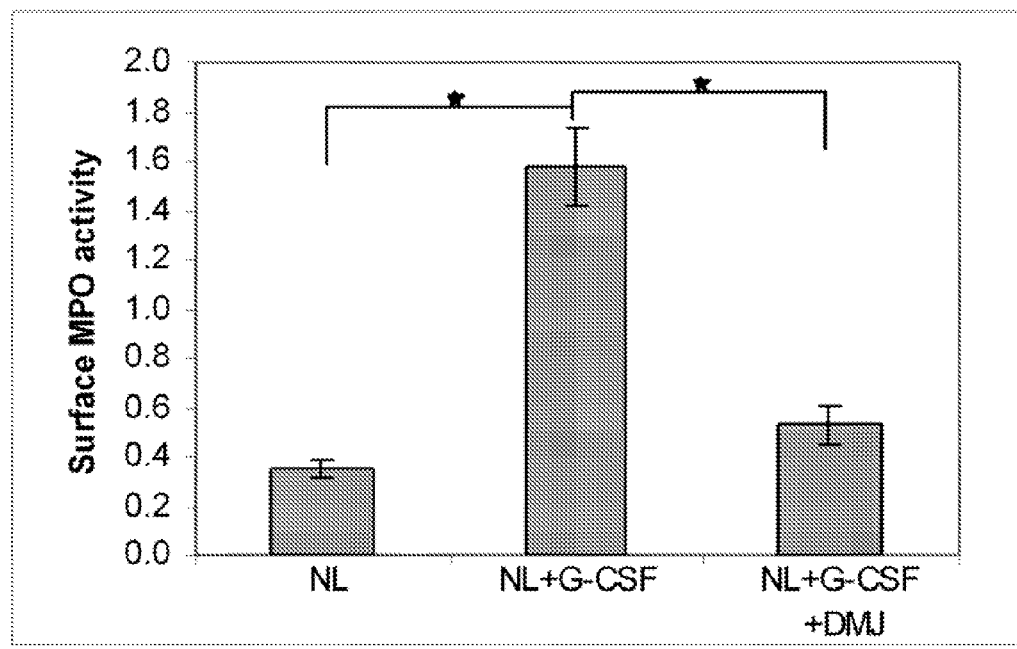
Figure 5H:
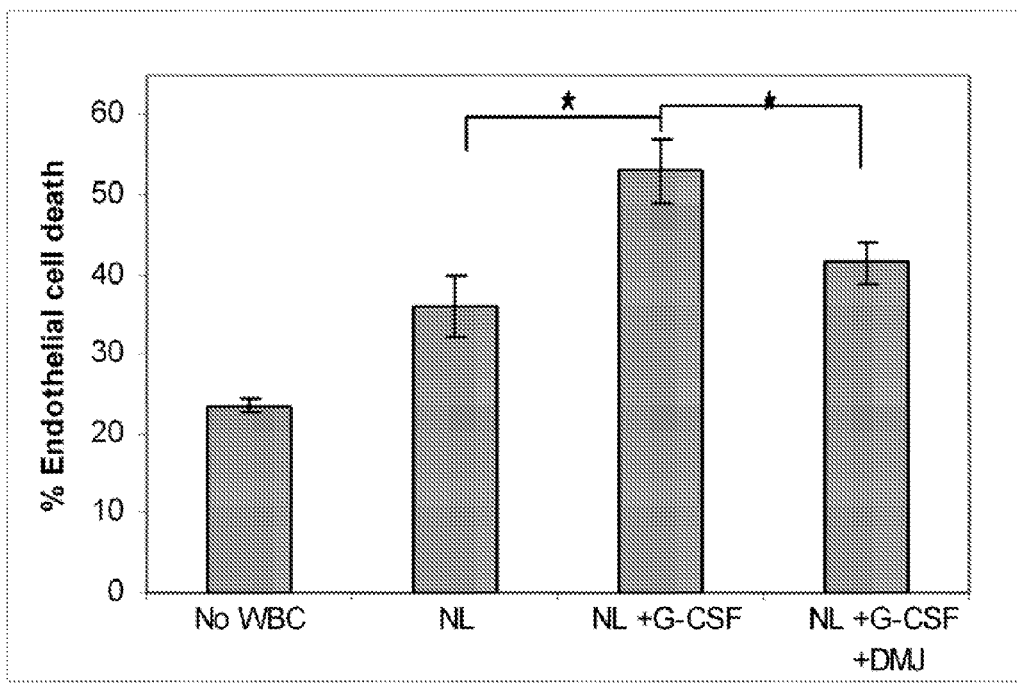

To evaluate the effect of G-CSF on cell surface MPO enzymatic activity, NL was placed in culture in presence (10 ng/ml) or absence of G-CSF for 48 hours. Cells were then surface-biotinylated, lysed, and membrane proteins were precipitated with streptavidin agarose beads. As shown in FIG. 5h, ex vivo G-CSF treatment induced surface peroxidase activity. Addition of DMJ to G-CSF-treated NL prevented induction of surface enzymatic activity (FIG. 5g). Upon incubation with stimulated HUVEC, NL treated with G-CSF showed an enhanced cytotoxic effect compared to that of untreated cells. Importantly, treatment with G-CSF and DMJ together prevented G-CSF-induced angiotoxicity (FIG. 5h).

Figure 6A:
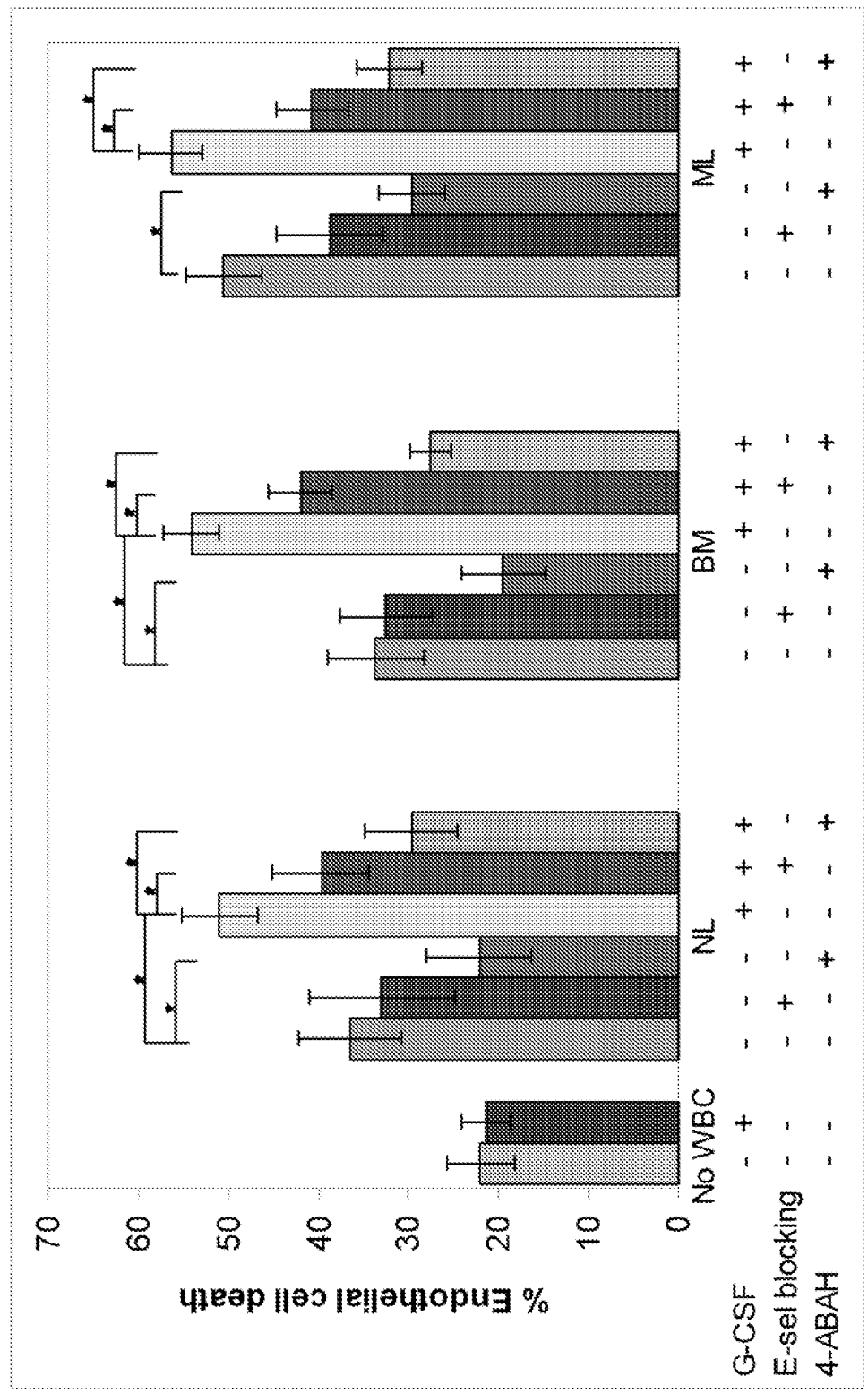
FIGS. 6 A-C. Interruption of E-selectin receptor/ligand interactions and MPO activity blunts angiotoxicity and myocardial injury. (A) Percentage endothelial cell death was evaluated in HUVEC monolayers in the presence (+) or absence (−) of G-CSF, without (no L) or in co-culture with myeloid cells (NL, BM or ML). Myeloid cell angiotoxicity was evaluated in the presence (+) or absence (−) of an E-selectin blocking antibody or of MPO inhibitor (4-ABAH). Values represent mean±SD of percent endothelial cell death from multiple donors (n>20), *p<0.05. (B) Evaluation of angiotoxicity in HUVEC monolayers in the absence or presence of sialidase or in the presence of ML or sialidase-treated ML. Values represent mean±SD of percent endothelial cell death from multiple donors (n=5), *p<0.05. (C) Relative change in the heart ejection fraction (EF) of induced-myocardial infarct mice injected with ML or sialidase-treated ML with respect to the heart ejection fraction of sham-operated counterpart mice injected with ML or sialidase-treated ML. Values represent mean±SD of percent EF change (n=3), *p<0.05.

G-CSF-induced myeloid cell angiotoxicity is blunted by blocking E-selectin receptor/ligand interactions or MPO enzymatic activity. To assess the effect of MPO-EL expression on endothelial viability, TNF-α-stimulated HUVEC were incubated with NL, BM or ML in the presence or absence of G-CSF. In all HUVEC cultures, endothelial cell death was markedly increased by co-incubation with ML or with G-CSF-treated NL or BM, when compared to untreated NL or BM cells (FIG. 6a). Notably, there was no significant increase in angiotoxicity with G-CSF-treated ML when compared to untreated ML. Concomitant incubation with an E-selectin function-blocking antibody reduced endothelial cell death in ML cultures and in NL or BM cultures treated with G-CSF. Importantly, incubation with 4-aminobenzoic hydrazide (4-ABAH), a specific MPO inhibitor, most effectively decreased endothelial cell death in all cultures (FIG. 6a).

Figure 6B:
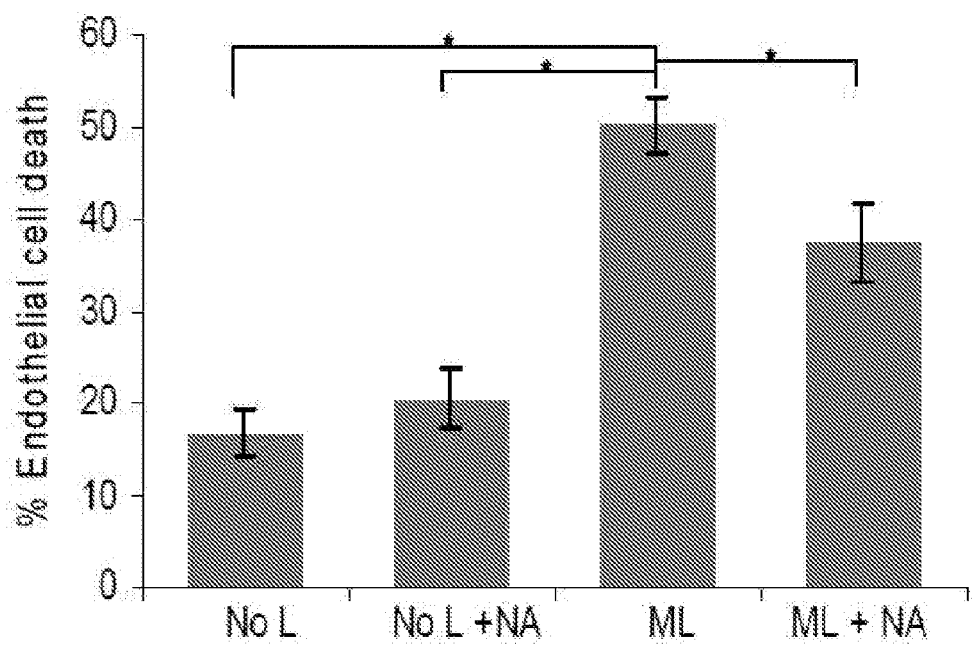
Figure 6C:
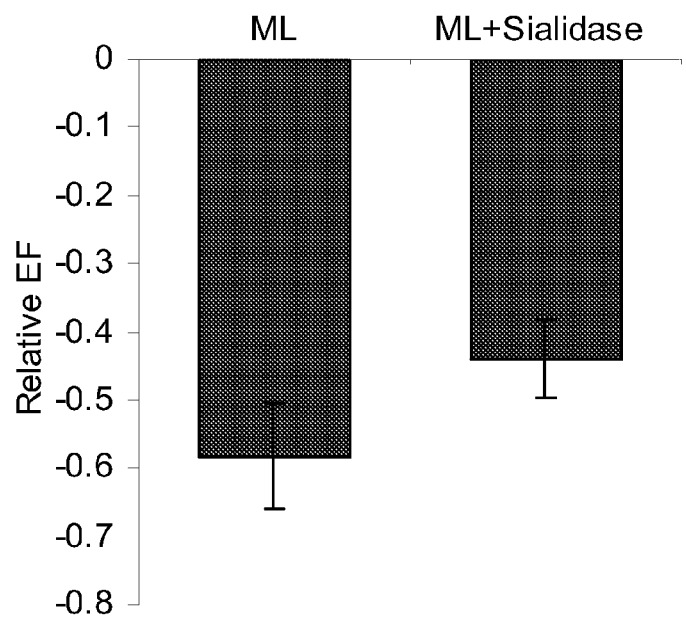

In an alternative approach, we abrogated E-selectin ligand activity by use of sialidase to cleave terminal sialic acid from sLex, the canonical E-selectin binding determinant. Incubation of endothelial cells with sialidase had no effect endothelial viability; however, co-culture of endothelial cells with ML treated with sialidase significantly decreased endothelial cell death compared to that in co-cultures of untreated ML (FIG. 6b). Since ML treated with neuraminidase exhibit decreased angiotoxicity, we assessed whether sialidase treatment of ML to disrupt E-selectin ligand activity would have a beneficial effect on recovery of heart function after myocardial infarct. To this end, ML or sialidase-treated ML were injected in mice within five hours after surgically-induced infarct. Notably, sialidase treatment did not affect the clearance of infused ML, as no differences in the levels of circulating cells were noted among treated and untreated ML (data not shown) for the first 24 hours after administration. Echocardiogram obtained 7 days post-MI showed improved ejection fraction in mice injected with neuraminidase-treated ML compared to that of mice injected with untreated ML (FIG. 6c).

Discussion

The known association of G-CSF administration and vascular complications prompted us to investigate whether G-CSF-stimulated myeloid cells alter vascular integrity. We observed that injection of G-CSF-mobilized human leukocytes (ML) accentuates cardiac injury in mice following myocardial ischemia. Also, ML displays heightened cytotoxicity to vascular endothelium which is blunted by interruption of E-selectin receptor/ligand interactions.

Our data indicate that the ~65 kDa E-selectin ligand comprises the heavy chain of a specialized, membrane-expressed glycoform of MPO, a well-characterized lysosomal enzyme whose synthesis is induced by G-CSF. MPO is initially expressed during promyelocyte development, and is characteristically stored in azurophilic granules of neutrophils, monocytes and macrophages. Mature MPO is a heme-containing glycoprotein of ~140 kDa which consists of two catalytically active monomers of ~75 kDa, each comprised of a 55-65 kDa heavy chain and a 10-15 kDa light chain, generated from a ~90 kDa precursor.

Cell surface presentation is essential for MPO-EL to function as an E-selectin ligand. Inhibition of N-glycan Golgi-processing with DMJ abrogated G-CSF-induced decoration of MPO with HECA452-reactive glycans, resulting in markedly reduced MPO membrane expression. DMJ did not eliminate the re-expression of E-selectin ligands following sialidase treatment; it only inhibited the boost in E-selectin ligand expression induced by G-CSF. DMJ does not affect processing of O-linked glycans, therefore any residual HECA-452 reactivity on the presence of DMJ reflects contribution(s) of O-sialofucosylated glycoproteins and glycolipids. Thus, through induction of relevant glycosyltransferases, G-CSF licenses sialofucosylations on N-linked carbohydrates and creates E-selectin ligands, including MPO-EL.

The precise mechanism(s) by which carbohydrate modifications target MPO expression on the cell membrane is uncharacterized at present. However, there is a well-known correlation between cell surface expression of glycoproteins and the N-linked glycosylation pathway which assures insertion and remodeling of correct carbohydrates on de novo synthesized glycoprotein during their transit through reticulum endoplastic (RE) and the Golgi. MPO biosynthesis follows a complex succession of proteolytic cleavages and glycan remodeling which directs this glycoprotein either to the azurophilic granules or to the extracellular space. It is believed that MPO can reach the azurophilic granules either by passing through the trans-Golgi into the late endosomes or by first being displayed on the plasma membrane followed by internalization into endosomes. Under physiological conditions, G-CSF induces MPO synthesis during development of myelocyte and monocyte precursors and stops as cells reach maturity. MPO synthesis can be reactivated in mature leukocytes. Hematopoietic stem/progenitor cell mobilization with clinical doses of G-CSF induces myeloid cell MPO-EL synthesis and its expression on plasma membrane positions this catalytically active enzyme in direct proximity to endothelial cells. Washing cells with high salt solutions (e.g., 1.5 M NaCl) or treatment with PI-PLC (to cleave GPI-anchors) did not release MPO from the cell surface, suggesting that this glycoprotein is membrane integrated.

The data presented here show for the first time that G-CSF promotes a dual function for MPO—as a cytotoxic effector and an E-selectin ligand—providing a unifying perspective on the pathobiology of G-CSF-induced vascular complications. Engagement of vascular E-selectin with corresponding ligands expressed on the surface of circulating cells Initiates decelerative contacts of circulating cells onto the target endothelium under hemodynamic flow conditions, thereby allowing for subsequent integrin-mediated firm adherence and extravasation. The ability of E-selectin to recruit leukocytes to sites of inflammation guarantees that the host defense arsenal is delivered to the correct "address". However, at the outset of recruitment, E-selectin-mediated MPO-EL binding to endothelium and consequent production of oxidizing agents would serve to affix toxic metabolites to the endothelium, thereby heightening vascular injury within inflamed tissue(s). Notably, sickle cell crises, coronary artery disease, atherosclerosis, and stroke, have all been linked to MPO. Moreover, MPO catalyzes oxidation of vascular nitric oxide (NO), resulting in consumption of NO and formation of highly reactive nitrite species which participate in deleterious protein tyrosine nitration. Endogenous NO is a critical anti-inflammatory and anti-atherogenic factor that inhibits endothelial activation and prevents leukocyte adhesion by suppressing expression of E-selectin induced by cytokines such as TNF-α. Thus, independent of direct cytotoxicity, through its enzymatic role in reducing NO bioavailability, MPO sustains expression of E-selectin on endothelial cells that further supports binding of leukocytes bearing E-selectin ligands such as MPO-EL. This loop would serve to compound vascular injury. Importantly, the fact that life-threatening sickle cell crisis is induced by G-CSF administration and, specifically, that anti-E-selectin agents can ameliorate this process, suggests a role for MPO-EL in this vasculopathy.

Within the past decade, several clinical trials using G-CSF to mobilize hematopoietic stem cells in patients with ischemic heart disease have been performed with the intent to improve myocardial function. Though generally safe, significant adverse vascular effects have been observed when G-CSF is administered to patients with coronary artery disease, especially in patients receiving G-CSF in the immediate peri-infarct period or in those with significant ischemic symptoms. Indeed, in post-MI patients receiving coronary stenting, an alarming rate of restenosis was observed in those patients that received G-CSF immediately prior to stenting. Our results showing that administration of human ML to mice following surgically-induced myocardial infarct augments myocardial injury, supporting these clinical observations. Notably, mice with infarcts that received ML treated with sialidase had relative preservation of ejection fraction, implicating a role for E-selectin ligand activity in the observed ML-associated myocardial compromise. These findings, coupled with data from in vitro studies showing that treatment of myeloid cells with G-CSF increases angiotoxicity which is reversed by blocking MPO activity and by disruption of E-selectin binding, directly link MPO-EL expression with endothelial injury, offering a new operational paradigm for MPO-associated pathobiology. Leukocyte surface MPO expression is already known to be associated with development of vasculitides such as Wegener's granulomatosis and Churg-Strauss syndrome. These conditions are characterized by expression of MPO on activated neutrophils which serves as an antigenic target for antineutrophil cytoplasm autoantibodies (ANCA). Notably, ANCA binding activates neutrophils, causing increased endothelial adhesion and angiotoxicity, and, specifically, G-CSF induces flares of ANCA-associated vasculitis. It is also well-known that MPC) and MPO-generated hypohalide products are concentrated in atherosclerotic lesions. These important clinical observations underscore the novel finding here that MPO, a major effector of cytotoxicity, is presented on the leukocyte surface, in a form that localizes this cytocidal agent in direct contact with endothelial cells. Thus, the results here focus new attention on the multipurpose role(s) of MPO in inflammatory conditions, and provide novel mechanistic insights on how interruption of E-selectin receptor/ligand interactions may serve to prevent G-CSF-induced vascular complications and, potentially, sickle cell crises, atherosclerosis, and ANCA-related vasculitic syndromes.

Materials and Methods

Cells. Human cells were obtained and used in accordance with the procedures approved by the Human Experimentation and Ethics Committees of Partners Cancer Care Institutions (Massachusetts General Hospital, Brigham and Women's Hospital, and Dana Farber Cancer Institute). ML were collected by blood apheresis from healthy donors receiving G-CSF to mobilize hematopoietic progenitors for hematopoietic stem cell transplantation (samples were provided by the Cell Manipulation Core Facility from Brigham and Women's Hospital/Dana Farber Cancer Institute). NL were isolated from blood obtained from healthy volunteers. Human BM cells were separated from filter sets used during bone marrow harvests performed at Massachusetts General Hospital. To ensure consistency in sample preparation and obtain data most relevant to native human biology, cells from blood and marrow samples were uniformly processed for relevant analyses within 2 hours of collection. The leukocytes from different sources were purified by direct centrifugal sedimentation or by Ficoll Histopaque®-1077 (Sigma-Aldrich, St. Louis, Mo.) separation and the residual red cells were eliminated by hypotonic lysis. Isolated cells were washed with phosphate buffered saline (PBS) and used in downstream procedures.

Antibodies. Western blot analysis was performed with the following antibodies: recombinant mouse E-selectin-human Fc chimera, (R&D Systems, Minneapolis, Minn.), horseradish peroxidase (HRP)-conjugated goat anti-human Ig, (Southern Biotech, Birmingham, Ala.), mouse monoclonal anti-MPO, clone 2C7 (Abcam, Cambridge, Mass.), goat anti-mouse IgG HRP-conjugated and streptavidin HRP-conjugated (BD Bioscience, San Jose, Calif.). Mouse anti-MPO mAb, clone 1A1 from Abcam (Cambridge, Mass.), was used for immunoprecipitations. Flow cytometry analysis was performed with the following antibodies: HECA-452 mAb (BD Bioscience, San Jose, Calif.); goat anti-rat IgM fluorescein isothiocyanate (FITC)-conjugated, rat IgM isotype, and mouse IgG isotype (Southern Biotech, Birmingham, Ala.); mouse anti-MPO mAb, clone 2C7 (Abcam, Cambridge, Mass.) and goat anti-mouse IgG phycoerythrin (PE)-conjugated (Santa Cruz Biotechnology, Santa Cruz, Calif.).

Immunoprecipitations, SDS-PAGE and Western Blotting. Leukocytes were lysed in Buffer A (0.5 mM Tris, pH=8, 150 mM NaCl, 20 μg/ml PMSF, 0.02% sodium azide) supplemented with 1% Triton (Sigma-Aldrich, St. Louis, Mo.) and protease inhibitor cocktail (Roche Diagnostics GmbH, Mannheim, Germany). Cell lysates were precleared with rProtein G Agarose beads (Invitrogen, Carlsbad, Calif.). Immunoprecipitations were performed at 4° C. for 16 h, by incubating the precleared lysates with 2 μg antibody and a fresh batch of agarose beads blocked in advance with 1 mg/ml bovine serum albumin (Sigma-Aldrich, St. Louis, Mo.). After extensive washes, the beads were boiled with sample buffer and the released antigens or cell lysates were resolved on 7.5% Tris-HCl SDS-PAGE (Criterion™ Precast Gel, Bio-Rad Laboratories, Hercules, Calif.). In western blot experiments separated proteins were transferred to Sequi-Blot™PVDF Membrane (Bio-Rad Laboratories, Hercules, Calif.) which was blocked for 2 h with a solution of 5% Non-Fat Milk (LabScientific, Livingston, N.J.). Proteins were detected with E-selectin-Ig chimera or with anti-MPO mAb: clone 2C7 (Abcam) and clone 3D3 (a generous gift from Carrie Rice at Maine Biotechnology Services, ME). Secondary antibodies goat anti-human IgG and goat anti-mouse IgG, HRP-conjugated were detected with Lumi-Light Western Blotting Substrate, (Roche Diagnostics GmbH, Mannheim, Germany).

Lectin chromatography and mass spectrometry analysis. Wheat germ agglutinin (WGA) lectin chromatography was employed to purify the glycoprotein pool of selectin ligands from ML. Cell lysates were incubated with WGA immobilized to agarose beads (Pierce, Rockford, Ill.) and, after extensive washes, the glycoproteins were released and dialyzed. Two 7.5% SDS-PAGE were run in parallel to resolve the selectin ligands. The proteins from one gel were transferred to a PVDF membrane which was stained in western blot with E-selectin Ig. The migration pattern of selectin ligands, revealed by western blot was used to locate the relevant proteins in the second gel. Thin slices were excised from the gel area where the selectin ligands migrated. Protein in-gel digestion was performed with proteomics grade trypsin (Sigma-Aldrich, St. Louis, Mo.) by covering the gel slices with trypsin solution (40 mM ammonium bicarbonate in 9% acetonitrile) and incubating at 37° C. for 16 h. Gel pieces were vortexed with 0.1% trifluoroacetic acid (Fluka) in 50% acetonitrile (Fisher Scientific, Pittsburgh, Pa.) to extract the peptides, which were further concentrated with a C18 Zip Tip (Millipore Corporation, Billerica, Mass.). The peptide mixture was analyzed with a MALDI-TOF mass spectrometer (Axima-CFR, Kratos-Shimadzu Biotech, Manchester, UK) using dihydroxybenzoic acid (DHB, 10 mg/mL) as matrix. The instrument was calibrated with a set of peptide standards (Proteomass MALDI-MS calibration kit, Sigma).

Cell surface biotinylation. Cells were washed with PBS and incubated with NHS-PEO$_4$-biotin (Pierce, Rockford, Ill.) or DMSO for negative control, as recommended in the manufacturer specifications. After 15 min at room temperature, cells were washed with PBS supplemented with non-essential amino acids followed by extensive wash with PBS. Biotinylation efficiency was monitored by cell surface staining with PE-conjugated streptavidin followed by flow cytometry analysis.

Flow cytometry. Cell surface expression of E-selectin ligands and MPO was determined by indirect single-color immunostaining with HECA-452 and anti-MPO (2C7) mAbs, respectively. Cells were incubated with primary antibodies and their matched isotype controls in PBS with 2% FBS for 20 min, on ice. After successive washes with PBS and 2% FBS cells were stained with FITC-conjugated secondary antibody for HECA-452 and PE-conjugated secondary antibody for MPO. Stained cells were then washed, resuspended in PBS, and analyzed using the Cytomics FC 500 MPL flow cytometer (Beckman Coulter, Miami, Fla.).

In vitro G-CSF treatment. Myeloid cells ($10^6$ cells/ml), isolated from different sources were cultured with RPMI 1640 medium (Mediatech, Inc, Manassas, Va.) with 10% FBS, 1% pen/strep and 10 ng/ml recombinant human G-CSF (Neupogen) from Amgen Mfg. Ltd., CA. Cells were maintained in culture for 72 h, at 37° C. and G-CSF aliquots were added after each 24 h period.

Neuraminidase and DMJ treatment. Cells were isolated from the buffy coat of bone marrow aspirates after centrifugal sedimentation and red blood cell lysis. Purified nucleated cells ($10^7$/ml) were incubated with *Vibrio Cholerae* neuraminidase (Roche Diagnostics GmbH, Mannheim, Germany), for 1 h at 37° C. Efficiency of sialic acid removal was confirmed by cell surface staining with HECA-452 mAb followed by flow cytometry analysis. After extensive washes, cells were divided in equal numbers and cultured in RPMI 1640 medium, for 48 h, with or without G-CSF treatment. In parallel, a subset of cells cultured with G-CSF was treated with 1 mM deoxymannojirimycin (DMJ). The effect(s) of G-CSF and DMJ were assessed by flow cytometry analysis of surface expression of HECA-452 determinants and of MPO.

Detection of membrane MPO activity. Aliquots of NL and ML were surface biotinylated, lyesed and membrane proteins were precipitated with streptavidin-conjugated agarose beads. The beads were incubated with a chromogenic peroxidase substrate, o-Phenylenediamine dihydrochloride (OPD) (Sigma) and the activity of surface MPO was monitored spectrophotometrically.

Endothelial cell death evaluation and inhibition of MPO activity assay. HUVECs were obtained from the Vascular Biology Core Facility of the Department of Pathology of Brigham and Women's Hospital and were grown on fibronectin (BD Bioscience) coated plates (20 μg/ml) with Medium 199 (Cambrex, East Rutherford, N.J.), supplemented with 20% FBS, 2 mM L-glutamine (Invitrogen), 1% pen/strep, 100 μg/ml heparin (Sigma) and 50 μg/ml endothelial cell growth supplement (Biomedical Technologies, Stoughton, Mass.). Endothelial cells were activated for 6 h in culture with 40 ng/ml TNFα to express E-selectin and incubation with 10 μg/ml mouse anti-human CD62E antibody (BD Pharmingen) was used to block E-selectin function. Leukocytes of different origins were treated with G-CSF or G-CSF and DMJ and co-cultured with activated HUVECs for 48 h. To inhibit MPO activity leukocytes were incubated with 100 μM 4-Aminobenzoic hydrazide (4-ABAH) (Sigma-Aldrich) in culture media for 48 h at 37° C. Endothelial cell death was quantified by trypan blue exclusion assay and the number of dead cells was reported as percentage from the number of total cells counted per squared unit of HUVEC layer.

Surgically induced myocardial infarct (MI) and echocardiographic measurements.

Adult RAG-2/JAK-3 SCID mice were maintained on a standard mouse chow diet and water ad libitum, and housed in a temperature-controlled environment under an alternating 12-hour light/dark cycle. All animal handling procedures adhered strictly to the approved guidelines of the Institutional Animal Care and Use Committee. Mice paired by weight and sex were distributed in two groups: in one group experimental MI was induced by permanent left anterior descending artery (LAD) ligation, as previously described[67] and another group that underwent open thoracotomy without coronary ligation (sham operated). Within five hours following the surgery, mice from each group were injected via jugular vein either with PBS or different cell types: NL, ML or sialidase-treated ML ($4 \times 10^6$ cells/mouse). The surgeon who performed the MI procedure and the jugular vein perfusions was blinded to the type of cells/PE3S injected in each animal. Echocardiography was performed on all mice before surgery (baseline), at 3 days and 7 days following surgery using an 18 to 38 MHz linear-array transducer with a digital ultrasound system (Vevo 2100 Imaging System, VisualSonics, Toronto, Canada). Standard parasternal long- and short-axis views were obtained during each echocardiographic examination and image measurements were performed offline by an investigator blinded to animal groups and the cell types/PBS injections.

PI-PLC cell treatment. ML ($1 \times 10^6$) were incubated in PBS with 1 unit of PI-PLC from *Bacillus cereus* (Molecular Probes, OR) for 30 min. at 4° C. To verify the enzyme efficiency cells were stained with anti-CD55 mAb, clone JS11 (BioLegend, CA) since CD55 is known to be attached to the hematopoietic cell membrane by a GPI-anchor. Cells were stained with anti-MPO mAB, clone 2C7 to verify whether MPO is GPI-anchored or with anti-CD44 mAb, clone 515 as negative control. Anti-mouse IgG-FITC was used as secondary antibody staining and cells were monitored by flow cytometry.

Washes with high salt solutions. Cells were washed with 0.5, 1 or 1.5 M NaCl by agitation at room temperature and quickly returned to PBS. Cell surface expression of MPO was monitored by staining with anti-MPO mAB, clone 2C7, anti-mouse IgG-FITC secondary antibody and flow cytometry analysis.

Statistical analysis. The compared values represent means of cell subsets isolated from random human clinical samples of multiple donors. The error bars represent standard deviation (SD). Statistical analysis was performed using a two-tailed, unpaired Student's t-test of the means. P values <0.05 were considered statistically significant.

REFERENCES

Elfenbein, G. J. & Sackstein, R. Primed marrow for autologous and allogeneic transplantation: a review comparing primed marrow to mobilized blood and steady-state marrow. Exp Hematol 32, 327-339 (2004).

Lindemann, A. & Rumberger, B. Vascular complications in patients treated with granulocyte colony-stimulating factor (G-CSF). Eur J Cancer 29A, 2338-2339 (1993).

Nervi, B., Link, D. C. & DiPersio, J. F. Cytokines and hematopoietic stem cell mobilization. J Cell Biochem 99, 690-705 (2006).

Fukumoto, Y., et al. Angina pectoris occurring during granulocyte colony-stimulating factor-combined preparatory regimen for autologous peripheral blood stem cell transplantation in a patient with acute myelogenous leukaemia. Br J Haematol 97, 666-668 (1997).

Hill, J. M., et al. Outcomes and risks of granulocyte colony-stimulating factor in patients with coronary artery disease. J Am Coll Cardiol 46, 1643-1648 (2005).

Fitzhugh, C. D., Hsieh, M. M., Bolan, C. D., Saenz, C. & Tisdale, J. F. Granulocyte colony-stimulating factor (G-CSF) administration in individuals with sickle cell disease: time for a moratorium? Cytotherapy 11, 464-471 (2009).

Tigue, C. C., et al. Granulocyte-colony stimulating factor administration to healthy individuals and persons with chronic neutropenia or cancer: an overview of safety considerations from the Research on Adverse Drug Events and Reports project. Bone Marrow Transplant 40, 185-192 (2007).

Becker, P. S., et al. Spontaneous splenic rupture following administration of granulocyte colony-stimulating factor (G-CSF): occurrence in an allogeneic donor of peripheral blood stem cells. Biol Blood Marrow Transplant 3, 45-49 (1997).

Dereure, O., Hillaire-Buys, D. & Guilhou, J. J. Neutrophil-dependent cutaneous side-effects of leucocyte colony-stimulating factors: manifestations of a neutrophil recovery syndrome? Br J Dermatol 150, 1228-1230 (2004).

Jain, K. K. Cutaneous vasculitis associated with granulocyte colony-stimulating factor. J Am Acad Dermatol 31, 213-215 (1994).

Iking-Konert, C., et al. Granulocyte colony-stimulating factor induces disease flare in patients with antineutrophil cytoplasmic antibody-associated vasculitis. J Rheumatol 31, 1655-1658 (2004).

Vasiliu, I. M., Petri, M. A. & Baer, A. N. Therapy with granulocyte colony-stimulating factor in systemic lupus erythematosus may be associated with severe flares. J Rheumatol 33, 1878-1880 (2006).

Xiao, B. G., Lu, C. Z. & Link, H. Cell biology and clinical promise of G-CSF: immunomodulation and neuroprotection. J Cell Mol Med 11, 1272-1290 (2007).

Yanqing, Z., Yu-Min, L., Jian, Q., Bao-Guo, X. & Chuan-Zhen, L. Fibronectin and neuroprotective effect of granulocyte colony-stimulating factor in focal cerebral ischemia. Brain Res 1098, 161-169 (2006).

Hamilton, J. A. Colony-stimulating factors in inflammation and autoimmunity. Nat Rev Immunol 8, 533-544 (2008).

Butcher, E. C. Leukocyte-endothelial cell recognition: three (or more) steps to specificity and diversity. Cell 67, 1033-1036 (1991).

Springer, T. A. Traffic signals on endothelium for lymphocyte recirculation and leukocyte emigration. Annu Rev Physiol 57, 827-872 (1995).

Sackstein, R. The lymphocyte homing receptors: gatekeepers of the multistep paradigm. Curr Opin Hematol 12, 444-450 (2005).

Fuhlbrigge, R. C., Kieffer, J. D., Armerding, D. & Kupper, T. S. Cutaneous lymphocyte antigen is a specialized form of PSGL-1 expressed on skin-homing T cells. Nature 389, 978-981 (1997).

Sackstein, R. The bone marrow is akin to skin: HCELL and the biology of hematopoietic stem cell homing. J Investig Dermatol Symp Proc 9, 215-223 (2004).

Dagia, N. M., et al. G-CSF induces E-selectin ligand expression on human myeloid cells. Nat Med 12, 1185-1190 (2006).

Babior, B. M., Kipnes, R. S. & Curnutte, J. T. Biological defense mechanisms. The production by leukocytes of superoxide, a potential bactericidal agent. J Clin Invest 52, 741-744 (1973).

Klebanoff, S. J. Myeloperoxidase. Proc Assoc Am Physicians 111, 383-389 (1999).

Lau, D. & Baldus, S. Myeloperoxidase and its contributory role in inflammatory vascular disease. Pharmacol Ther 111, 16-26 (2006).

Malle, E., Buch, T. & Grone, H. J. Myeloperoxidase in kidney disease. Kidney Int 64, 1956-1967 (2003).

Hazen, S. L. & Heinecke, J. W. 3-Chlorotyrosine, a specific marker of myeloperoxidase-catalyzed oxidation, is markedly elevated in low density lipoprotein isolated from human atherosclerotic intima. J Clin Invest 99, 2075-2081 (1997).

Falk, R. J., Terrell, R. S., Charles, L. A. & Jennette, J. C. Anti-neutrophil cytoplasmic autoantibodies induce neutrophils to degranulate and produce oxygen radicals in vitro. Proc Natl Acad Sci USA 87, 4115-4119 (1990).

Kallenberg, C. G. Pathophysiology of ANCA-associated small vessel vasculitis. Curr Rheumatol Rep 12, 399-405.

Fuste, B., et al. Granulocyte colony-stimulating factor increases expression of adhesion receptors on endothelial cells through activation of p38 MAPK. Haematologica 89, 578-585 (2004).

Ohsaka, A., Saionji, K. & Igari, J. Granulocyte colony-stimulating factor administration increases serum concentrations of soluble selectins. Br J Haematol 100, 66-69 (1998).

Tsuruta, T., Tani, K., Hoshika, A. & Asano, S. Myeloperoxidase gene expression and regulation by myeloid cell growth factors in normal and leukemic cells. Leuk Lymphoma 32, 257-267 (1999).

Allen, R. C., Stevens, P. R., Price, T. H., Chatta, G. S. & Dale, D. C. In vivo effects of recombinant human granulocyte colony-stimulating factor on neutrophil oxidative functions in normal human volunteers. J Infect Dis 175, 1184-1192 (1997).

Falanga, A., et al. Neutrophil activation and hemostatic changes in healthy donors receiving granulocyte colony-stimulating factor. Blood 93, 2506-2514 (1999)

Cella, G., et al. Blood oxidative status and selectins plasma levels in healthy donors receiving granulocyte-colony stimulating factor. Leukemia 20, 1430-1434 (2006).

Kang, H. J., et al. Effects of intracoronary infusion of peripheral blood stem-cells mobilised with granulocyte-colony stimulating factor on left ventricular systolic function and restenosis after coronary stenting in myocardial infarction: the MAGIC cell randomised clinical trial. Lancet 363, 751-756 (2004).

Eckman, P. M., Bertog, S. C., Wilson, R. F. & Henry, T. D. Ischemic cardiac complications following G-CSF. Catheter Cardiovasc Interv 76, 98-101.

Faulkner, L. B., et al. G-CSF serum pharmacokinetics during peripheral blood progenitor cell mobilization: neutrophil count-adjusted dosage might potentially improve mobilization and be more cost-effective. Bone Marrow Transplant 21, 1091-1095 (1998).

Handa, K., Stroud, M. R. & Hakomori, S. Sialosyl-fucosyl Poly-LacNAc without the sialosyl-Lex epitope as the physiological myeloid cell ligand in E-selectin-dependent adhesion: studies under static and dynamic flow conditions. Biochemistry 36, 12412-12420 (1997).

Nimrichter, L., et al. E-selectin receptors on human leukocytes. Blood 112, 3744-3752 (2008).

Berliner, N., et al. Granulocyte colony-stimulating factor induction of normal human bone marrow progenitors results in neutrophil-specific gene expression. Blood 85, 799-803 (1995).

Sato, N., Kashima, K., Tanaka, Y., Shimizu, H. & Mori, M. Effect of granulocyte-colony stimulating factor on generation of oxygen-derived free radicals and myeloperoxidase activity in neutrophils from poorly controlled NIDDM patients. Diabetes 46, 133-137 (1997).

Bainton, D. F., Ullyot, J. L. & Farquhar, M. G. The development of neutrophilic polymorphonuclear leukocytes in human bone marrow. J Exp Med 134, 907-934 (1971).

Stromberg, K., Persson, A. M. & Olsson, I. The processing and intracellular transport of myeloperoxidase. Modulation by lysosomotropic agents and monensin. Eur J Cell Biol 39, 424-431 (1986).

Koeffler, H. P., Ranyard, J. & Pertcheck, M. Myeloperoxidase: its structure and expression during myeloid differentiation. Blood 65, 484-491 (1985).

Akin, D. T. & Kinkade, J. M., Jr. Processing of a newly identified intermediate of human myeloperoxidase in isolated granules occurs at neutral pH. J Biol Chem 261, 8370-8375 (1986).

Hansson, M., Olsson, I. & Nauseef, W. M. Biosynthesis, processing, and sorting of human myeloperoxidase. Arch Biochem Biophys 445, 214-224 (2006).

Ihrke, G., Kyttala, A., Russell, M. R., Rous, B. A. & Luzio, J. P. Differential use of two AP-3-mediated pathways by lysosomal membrane proteins. Traffic 5, 946-962 (2004).

Reynolds, W. F., et al. Myeloperoxidase polymorphism is associated with gender specific risk for Alzheimer's disease. Exp Neurol 155, 31-41 (1999).

Saleh, A. W., Hillen, H. F. & Duits, A. J. Levels of endothelial, neutrophil and platelet-specific factors in sickle cell anemia patients during hydroxyurea therapy. Acta Haematol 102, 31-37 (1999).

Baldus, S., et al. Myeloperoxidase serum levels predict risk in patients with acute coronary syndromes. Circulation 108, 1440-1445 (2003).

Zhang, R., et al. Association between myeloperoxidase levels and risk of coronary artery disease. JAMA 286, 2136-2142 (2001).

Hazell, L. J., et al. Presence of hypochlorite-modified proteins in human atherosclerotic lesions. J Clin Invest 97, 1535-1544 (1996).

Malle, E., et al. Immunohistochemical evidence for the myeloperoxidase/H2O2/halide system in human atherosclerotic lesions: colocalization of myeloperoxidase and hypochlorite-modified proteins. Eur J Biochem 267, 4495-4503 (2000).

Daugherty, A., Dunn, J. L., Rateri, D. L. & Heinecke, J. W. Myeloperoxidase, a catalyst for lipoprotein oxidation, is expressed in human atherosclerotic lesions. J Clin Invest 94, 437-444 (1994).

Breckwoldt, M. O., et al. Tracking the inflammatory response in stroke in vivo by sensing the enzyme myeloperoxidase. Proc Natl Acad Sci USA 105, 18584-18589 (2008).

Eiserich, J. P., et al. Myeloperoxidase, a leukocyte-derived vascular NO oxidase. Science 296, 2391-2394 (2002).

Eiserich, J. P., et al. Formation of nitric oxide-derived inflammatory oxidants by myeloperoxidase in neutrophils. Nature 391, 393-397 (1998).

De Caterina, R., et al. Nitric oxide decreases cytokine-induced endothelial activation. Nitric oxide selectively reduces endothelial expression of adhesion molecules and proinflammatory cytokines. J Clin Invest 96, 60-68 (1995).

Kubes, P., Suzuki, M. & Granger, D. N. Nitric oxide: an endogenous modulator of leukocyte adhesion. Proc Natl Acad Sci USA 88, 4651-4655 (1991).

Chang, J., et al. GMI-1070, a novel pan-selectin antagonist, reverses acute vascular occlusions in sickle cell mice. Blood (2010).

Ellis, S. G., et al. Granulocyte colony stimulating factor in patients with large acute myocardial infarction: results of a pilot dose-escalation randomized trial. Am Heart J 152, 1051 e1059-1014 (2006).

Falk, R. J. & Jennette, J. C. Anti-neutrophil cytoplasmic autoantibodies with specificity for myeloperoxidase in patients with systemic vasculitis and idiopathic necrotizing and crescentic glomerulonephritis. N Engl J Med 318, 1651-1657 (1988).

Tervaert, J. W., et al. Detection of autoantibodies against myeloid lysosomal enzymes: a useful adjunct to classification of patients with biopsy-proven necrotizing arteritis. Am J Med 91, 59-66 (1991).

Bansal, P. J. & Tobin, M. C. Neonatal microscopic polyangiitis secondary to transfer of maternal myeloperoxidase-antineutrophil cytoplasmic antibody resulting in neonatal pulmonary hemorrhage and renal involvement. Ann Allergy Asthma Immunol 93, 398-401 (2004).

Csernok, E., Ernst, M., Schmitt, W., Bainton, D. F. & Gross, W. L. Activated neutrophils express proteinase 3 on their plasma membrane in vitro and in vivo. Clin Exp Immunol 95, 244-250 (1994).

Savige, J. A., et al. Anti-neutrophil cytoplasm antibodies in rheumatoid arthritis. Clin Exp Immunol 86, 92-98 (1991).

Bauer, M., et al. Echocardiographic speckle-tracking based strain imaging for rapid cardiovascular phenotyping in mice. Circ Res 108, 908-916.

What is claimed is:

1. A method for preventing and/or treating G-CSF-induced vascular complications and associated tissue damage comprising administering an anti-MPO-EL antibody that specifically binds to MPO-EL to a subject in need thereof, wherein the compound is administered in conjunction with G-CSF therapy.

2. The method of claim 1, wherein the compound is administered prior to, during or after administration of G-CSF.

3. A method for preventing and/or treating vascular complications and associated tissue damage comprising administering an anti-MPO-EL antibody that specifically binds to MPO-EL to a subject in need thereof.

4. The method of claim 3, wherein the vascular complication is sepsis.

5. The method of claim 3, wherein the vascular complication is leukocytoclastic vasculitis.

6. The method of claim 3, wherein the vascular complication is stroke.

7. The method of claim 3, wherein the vascular complication is angina pectoris.

8. The method of claim 3, wherein the vascular complication is myocardial infarct.

9. The method of claim 3, wherein the vascular complication is a localized or systemic vasculitis syndromes.

10. The method of claim 3, wherein the vascular complication is atherosclerosis.

11. The method of claim 3, wherein the vascular complication is Wegener's granulomatosis.

12. The method of claim 3, wherein the vascular complication is sickle cell crises.

13. A method of treating acute myocardial infarction or other ischemic events in conjunction with reperfusion therapy comprising administering an anti-MPO-EL antibody that specifically binds to MPO-EL to a subject in need thereof.

14. The method of claim 13, wherein the reperfusion therapy is primary angioplasty.

* * * * *